United States Patent
Okada

(10) Patent No.: US 6,528,187 B1
(45) Date of Patent: Mar. 4, 2003

(54) MATERIAL FOR LUMINESCENCE ELEMENT AND LUMINESCENCE ELEMENT USING THE SAME

(75) Inventor: Hisashi Okada, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/391,156

(22) Filed: Sep. 8, 1999

(30) Foreign Application Priority Data

Sep. 8, 1998 (JP) .......................... 10-254147

(51) Int. Cl.⁷ .................. H05B 33/14; C07D 221/02
(52) U.S. Cl. .................. 428/690; 428/704; 428/917; 428/323; 428/328; 428/213; 313/504; 313/506; 252/301.16; 252/301.26; 546/112; 546/152; 546/171
(58) Field of Search ................ 428/690, 704, 428/917, 323, 328, 213; 313/504, 506; 252/301.16, 301.26; 546/112, 152, 171

(56) References Cited

U.S. PATENT DOCUMENTS 3,920,690 A  * 11/1975 Harrington et al. ......... 260/310
5,747,183 A  *  5/1998 Shi et al. .................... 428/690

FOREIGN PATENT DOCUMENTS

JP       A-2-255790       10/1990

* cited by examiner

*Primary Examiner*—John J. Zimmerman
*Assistant Examiner*—Ling Xu
(74) *Attorney, Agent, or Firm*—Sughrue Mion, PLLC

(57) ABSTRACT

A material for a luminescence element is described, which is a compound having a partial structure represented by the following formula (I):

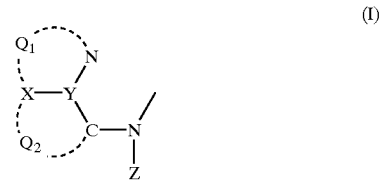

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_2R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group.

7 Claims, No Drawings

MATERIAL FOR LUMINESCENCE ELEMENT AND LUMINESCENCE ELEMENT USING THE SAME

FIELD OF THE INVENTION

The present invention relates to materials for a luminescence element which can emit light by converting electric energy to light (e.g., an organic electroluminescence (EL) element) and relates to the luminescence element, and in particular, the present invention relates to a luminescence element which can be suitably used in various fields such as display elements, displays, back lights, electrophotography, illumination light sources, recording light sources, reading light sources, indicators, signboards, interior design, etc.

BACKGROUND OF THE INVENTION

In recent years, various display elements have been researched and developed actively. Above all, organic EL elements can give high luminance at low voltage and have attracted public attention as promising display elements. For example, an EL element in which an organic thin film is formed by vapor deposition of an organic compound is known (*Applied Physics Letters*, Vol. 51, p. 913 (1987)). As compared with conventionally used single layer type elements, luminous characteristics of the organic EL element described in the above literature have been drastically improved by laminating tris (8-hydroxyquinolinate) aluminum complex (Alq) as an electron-transporting material with a hole-transporting material (an amine compound).

A method of doping a fluorescent dye is known as a means for further improving luminous efficiency of the above laminate type EL element. For example, the luminous efficiency of the organic EL element doped with a coumarin dye as described in *Journal of Applied Physics*, Vol. 65, p. 3610 (1989) has been widely improved as compared with elements which are not doped. In this case, light having a desired wavelength can be taken out by varying the kind of the fluorescent compound to be used. However, in the case where Alq is used as an electron-transporting material, if driving voltage is increased to obtain high luminance, green emission of Alq comes to be observed in addition to the emission of the doped fluorescent compound, as a result, there arises such a problem as color purity in the case of blue or red emission is reduced. Therefore, the development of host materials which do not generate color purity reduction has been desired.

Although organic EL elements which so far have been developed are certainly improved in light emission intensity and durability by the improvement of the constitution of elements and materials, they do not have sufficient performances yet considering various developments of applications. For example, conventional metal complexes, such as Alq, are chemically labile at electroluminescence, and inferior in adhesion to the cathode, and the problem of deterioration of elements has not yet been solved. Moreover, in the case of Alq, as it is a complex having oxine as a ligand, there is some fear in the safety of the material. Therefore, development of the electron-transporting materials of organic EL elements which are environmentally benign has been required.

On the other hand, it is a laminated element that has realized high luminance emission in an organic EL element byvacuum deposition of organic materials, but the production of elements by a coating system is preferred from the viewpoint of simplification of producing step, processability and realization of large area elements. However, elements which so far have been produced by a coating system are inferior to those produced by a vacuum deposition system in luminance and luminous efficiency, therefore, high luminance and luminescence with high efficiency have been left as problems to be solved.

SUMMARY OF THE INVENTION

A first object of the present invention is to provide a material for a luminescence element which shows good luminous characteristics and is excellent in stability by repeating use and a luminescence element.

A second object of the present invention is to provide a luminescence element which is excellent in color purity and a material for the luminescence element which makes it possible.

These objects of the present invention have been achieved the following means.

(1) A material for a luminescence element, which is a compound represented by the following formula (K-Ic), (K-Id) or K-Ie):

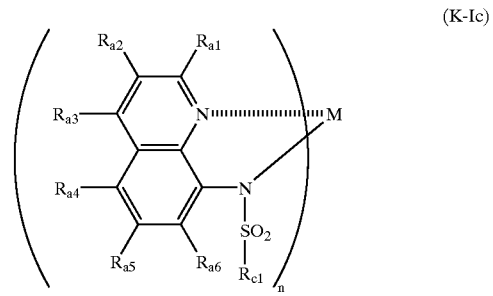

wherein $R_{a1}$ represent an aliphatic hydrocarbon group having 6 or less carbon atoms, an arly group, or a heterocyclic group; M represents a metal ion; n represents an integer of from 1 to 4; and $R_{a1}$, $R_{a2}$, $R_{a3}$, $R_{a4}$, $R_{a5}$ and $R_{a6}$ each represents a hydrogen atom or a substituent;

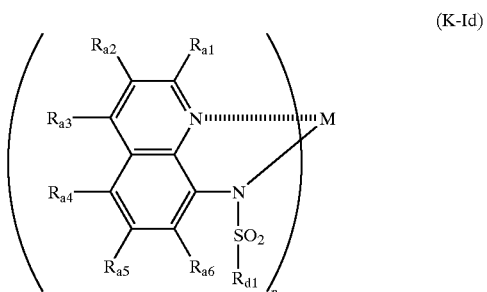

wherein $R_{a1}$ represents an aliphatic hydrocarbon group having from 9 to 30 carbon atoms, an aryl group, or a heterocyclic group; M represents a metal ion; n represents an integer of from 1 to 4; and $R_{a1}$, $R_{a2}$, R$a3$, $R_{a4}$, $R_{a5}$ and $R_{a6}$ each represents a hydrogen atom or a substituent; or

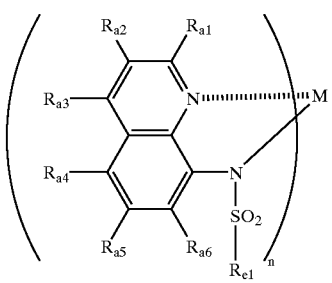

(K-Ie)

wherein $R_{a1}$ represents an aliphatic hydrocarbon group, an aryl group, or a heterocyclic group, each of which has a halogen atom, an alkoxyl group, an aryloxy group or a heterocyclic oxy group as a substituent; M represents a metal ion; n represents an integer of from 1 to 4; and $R_{a1}$, $R_{a2}$, $R_{a3}$, $R_{a4}$, $R_{a5}$ and $R_{a6}$ each represents a hydrogen atom or a substituent.

(2) The material for a luminescence element as in the above item (1), wherein said compound contains a divalent, trivalent, or tetravalent metal ion.

(3) The material for a luminescence element as in the above item (1), wherein said compound contains a zinc ion.

(4) A material for a luminescence element which is a compound having a partial structure represented by the following formula (I):

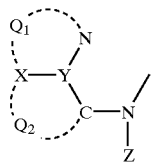

(I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_1R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group, wherein said compound is negative in "Reverse-Mutation Assay in Bacteria" provided by "Law Concerning the Examination and Regulation of Manufacture, etc., of Chemical Substances".

(5) A material for a luminescence element which is a compound having a partial structure represented by the following formula (I):

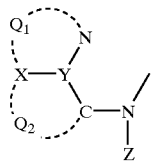

(I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_2R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group, wherein said compound has a glass transition temperature of 130° C. or more.

(6) A luminescence element comprising a pair of electrodes having formed therebetween a luminescence layer or a plurality of organic compound thin film layers comprising a luminescence layer, wherein at least one layer is a layer containing the material for a luminescence element described in the above item (1), (2), (3), (4) or (5).

(7) A luminescence element comprising a pair of electrodes having formed therebetween a luminescence layer or a plurality of organic compound thin film layers comprising a luminescence layer, wherein at least one layer is a layer formed by coating a compound having a partial structure represented by the following formula (I):

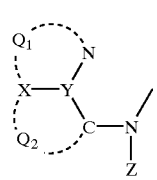

(I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_2R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group.

(8) A luminescence element comprising a pair of electrodes having formed therebetween a luminescence layer or a plurality of organic compound thin film layers comprising a luminescence layer, wherein at least one layer is a layer comprising a compound having a partial structure represented by the following formula (I):

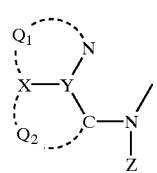

(I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_2R_1$, $COR_2$ or $POR_3(R4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group, having been dispersed in a polymer.

(9) A luminescence element comprising a pair of electrodes having formed therebetween a luminescence layer or a plurality of organic compound thin film layers comprising a luminescence layer, wherein at least one layer contains a compound having a partial structure represented by the following formula (I):

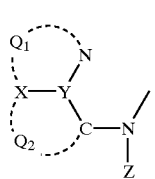

(I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_2R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group, wherein the layer containing said compound further contains at least one kind of other fluorescent compound.

(10) A luminescence element comprising a pair of electrodes having formed therebetween a luminescence layer or a plurality of organic compound thin film layers comprising a luminescence layer, wherein the organic compound thin film layers comprise at least three layers of a hole-transporting layer, a luminescence layer and an electron-transporting layer, said electron-transporting layer comprising at least a compound having a partial structure represented by the following formula (I):

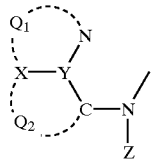

(I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; and Z represents $SO_1R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group.

(11) The luminescence element as in the above item (10), wherein the electron-transporting layer has a film thickness of from 1 to 80 nm.

(12) The luminescence element as in the above item (10), wherein the luminescence layer comprises a single compound.

(13) The luminescence element as in the above item (7), wherein said compound is a metal complex having a compound having a partial structure represented by formula (I) as a ligand.

(14) The luminescence element as in the above item (7), wherein said compound is a metal complex represented by the following formula (K-I):

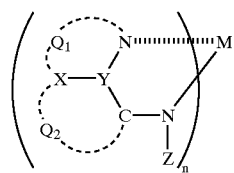

(K-I)

wherein $Q_1$ represents an atomic group necessary to form a 5- or 6-membered nitrogen-containing aromatic heterocyclic ring; $Q_2$ represents an atomic group necessary to form a 5- or 6-membered aromatic ring; X and Y each represents a carbon atom or a nitrogen atom; Z represents $SO_2R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group; M represents a metal ion; and n represents an integer of from 1 to 4.

(15) The luminescence element as in the above item (7), wherein said compound is a metal complex represented by the following formula (K-Ia):

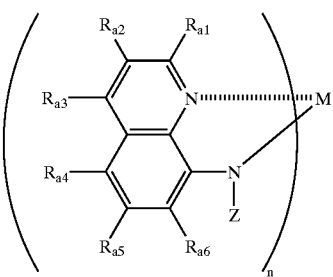

(K-Ia)

wherein Z represents $SO_2R_1$, $COR_2$ or $POR_3(R_4)$, wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group; M represents a metal ion; n represents an integer of from 1 to 4; and $R_{a1}$, $R_{a2}$, $R_{a3}$, $R_{a4}$, $R_{a5}$ and $R_{a6}$ each represents a hydrogen atom or a substituent.

(16) The luminescence element as in the above item (7), wherein said compound is represented by the following formula

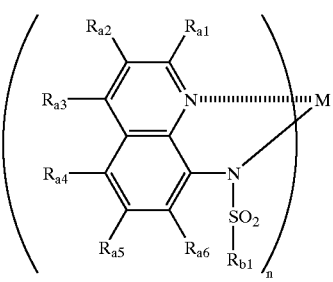

(K-Ib)

wherein $R_{b1}$ represents an aliphatic hydrocarbon group, an aryl group, or a heterocyclic group; M represents a metal ion; n represents an integer of from 1 to 4; and $R_{a1}$, $R_{a2}$, $Ra3$, $R_{a4}$, $R_{a5}$ and $R_{a6}$ each represents a hydrogen atom or a substituent.

DETAILED DESCRIPTION OF THE INVENTION

The present invention is described in detail below.

In the first place, the compound which has a partial structure represented by formula (I) is described.

$Q_1$ represents an atomic group necessary to form a 5- or 6-membered nitrogen-containing aromatic heterocyclic ring. Examples of 5- or 6-membered nitrogen-containing aromatic heterocyclic ring include pyrrole, imidazole, pyrazole, pyridine, pyrazine, pyrimidine, pyridazine, thiazole, isothiazole, oxazole, isoxazole, selenazole, and triazine, preferably pyridine, pyrazine, pyrimidine, and pyridazine, more preferably pyridine and pyrazine, and particularly preferably pyridine.

The 5- or 6-membered nitrogen-containing aromatic heterocyclic ring represented by $Q_1$ may have a substituent. Examples of substituents include, e.g., an alkyl group (preferably having from 1 to 30, more preferably from 1 to 20, and particularly preferably from 1 to 10, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably having from 2 to 30, more preferably from 2 to 20, and particularly preferably from 2 to 10, carbon atoms, e.g., vinyl, allyl, 2-butenyl, 3-pentenyl), an alkynyl group (preferably having from 2 to 30, more preferably from 2 to 20, and particularly preferably from 2 to 10, carbon atoms, e.g., propargyl, 3-pentynyl), an aryl group (preferably having from 6 to 30, more preferably from 6 to 20, and particularly preferably from 6 to 12, carbon atoms, e.g., phenyl, p-methylphenyl, naphthyl), an amino group (preferably having from 0 to 30, more preferably from 0 to 20, and particularly preferably from 0 to 10, carbon atoms, e.g., amino, methylamino, dimethylamino, diethylamino, dibenzylamino, diphenylamino, ditolylamino), an alkoxyl group (preferably having from 1 to 30, more preferably from 1 to 20, and particularly preferably from 1 to 10, carbon atoms, e.g., methoxy, ethoxy, butoxy, 2-ethylhexyloxy), an aryloxy group (preferably having from 6 to 30, more preferably from 6 to 20, and particularly preferably from 6 to 12, carbon atoms, e.g., phenyloxy, 1-naphthyloxy, 2-naphthyloxy), an acyl group (preferably having from 1 to 30, more preferably from 1 to 20, and particularly preferably from 1 to 12, carbon atoms, e.g., acetyl, benzoyl, formyl, pivaloyl), an alkoxycarbonyl group (preferably having from 2 to 30, more preferably from 2 to 20, and particularly preferably from 2 to 12, carbon atoms, e.g., methoxycarbonyl, ethoxycarbonyl), an aryloxycarbonyl group (preferably having from 7 to 30, more preferably from 7 to 20, and particularly preferably from 7 to 12, carbon atoms, e.g., phenyloxycarbonyl), an acyloxy group (preferably having from 2 to 30, more preferably from 2 to 20, and particularly preferably from 2 to 10, carbon atoms, e.g., acetoxy, benzoyloxy), an acylamino group (preferably having from 2 to 30, more preferably from 2 to 20, and particularly preferably from 2 to 10, carbon atoms, e.g., acetylamino, benzoylamino), an alkoxycarbonylamino group (preferably having from 2 to 30, more preferably from 2 to 20, and particularly preferably from 2 to 12, carbon atoms, e.g., methoxycarbonylamino), an aryloxycarbonylamino group (preferably having from 7 to 30, more preferably from 7 to 20, and particularly preferably from 7 to 12, carbon atoms, e.g., phenyloxycarbonylamino), a sulfonylamino group (preferably having from 1 to 30, more preferably from 1 to 20, and particularly preferably from 1 to 12, carbon atoms, e.g., methanesulfonylamino, benzenesulfonylamino), a sulfamoyl group (preferably having from 0 to 30, more preferably from 0 to 20, and particularly preferably from 0 to 12, carbon atoms, e.g., sulfamoyl, methylsulfamoyl, dimethylsulfamoyl, phenylsulfamoyl), a carbamoyl group (preferably having from 1 to 30, more preferably from 1 to 20, and particularly preferably from 1 to 12, carbon atoms, e.g., carbamoyl, methylcarbamoyl, diethylcarbamoyl, phenylcarbamoyl), an alkylthio group (preferably having from 1 to 30, more preferably from 1 to 20, and particularly preferably from 1 to 12, carbon atoms, e.g., methylthio, ethylthio), an arylthio group (preferably having from 6 to 30, more preferably from 6 to 20, and particularly preferably from 6 to 12, carbon atoms, e.g., phenylthio), a sulfonyl group (preferably having from 1 to 30, more preferably from 1 to 20, and particularly preferably from 1 to 12, carbon atoms, e.g., mesyl, tosyl), a sulfinyl group (preferably having from 1 to 30, more preferably from 1 to 20, and particularly preferably from 1 to 12, carbon atoms, e.g., methanesulfinyl, benzenesulfinyl), a ureido group (preferably having from 1 to 30, more preferably from 1 to 20, and particularly preferably from 1 to 12, carbon atoms, e.g., ureido, methylureido, phenylureido), a phosphoric acid amido group (preferably having from 1 to 30, more preferably from 1 to 20, and particularly preferably from 1 to 12, carbon atoms, e.g., diethylphosphoric acid amido, phenylphosphoric acid amido), a hydroxyl group, a mercapto group, ahalogenatom (e.g., fluorine, chlorine, bromine, iodine), a cyano group, a sulfo group, a carboxyl group, a nitro group, a hydroxamic acid group, a sulfino group, ahydrazino group, an imino group, a heterocyclic group (preferably having from 1 to 30, and more preferably from 1 to 12, carbon atoms, as hetero atoms, e.g., nitrogen, oxygen, sulfur can be exemplified, specifically, imidazolyl, pyridyl, quinolyl, furyl, piperidyl, morpholino, benzoxazolyl, benzimidazolyl, benzothiazolyl can be exemplified) and a silyl group (preferably having from 3 to 40, more preferably from 3 to 30, and particularly preferably from 3 to 24, carbon atoms, e.g., trimethylsilyl, triphenylsilyl). These substituents may further be substituted. When there are two or more substituents, they may be the same or different. Substituents may be linked to each other to form a ring, if possible.

Preferred examples of substituents include an alkyl group, an alkenyl group, an alkynyl group, an aryl group, an amino group, an alkoxyl group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, a carboxyl group, and a heterocyclic group, more preferred substituents include an alkyl group, an alkenyl group, an aryl group, a halogen atom, a cyano group, and a heterocyclic group, still more preferred substituents include an alkyl group, an alkenyl group, an aryl group, and a heterocyclic group, and particularly preferred substituents are an alkyl group, an alkenyl group, an aryl group, and an aromatic heterocyclic group.

$Q_2$ represents an atomic group necessary to form a 5- or 6-membered aromatic ring. The aromatic ring formed by $Q_2$ is an aryl group or an aromatic heterocyclic group, e.g., benzene, pyrrole, imidazole, pyrazole, pyridine, pyrazine, pyrimidine, pyridazine, thiazole, isothiazole, oxazole, isoxazole, selenazole, and triazine, preferably benzene, pyridine, pyrazine, pyrimidine, and pyridazine, more preferably benzene and pyridine, and particularly preferably benzene.

The 5- or 6-membered aromatic ring represented by $Q_2$ may have a substituent. The same groups described as substituents for $Q_1$ can be applied to substituents for $Q_2$ and preferred range is also the same. Substituents may be linked to each other to form a ring, if possible.

X and Y each represents a carbon atom or a nitrogen atom. Preferably, at least either of X or Y represents a carbon atom, more preferably both X and Y represent a carbon atom, or X represents a nitrogen atom and Y represents a carbon atom, and still more preferably both X and Y represent a carbon atom.

Z represents $SO_2R_1$, $COR_2$ or $POR_3(R_4)$ (wherein $R_1$, $R_2$, $R_3$ and $R_4$ each represents an aliphatic hydrocarbon group, an aryl group, a heterocyclic group, an amino group, an alkoxyl group, an aryloxy group or a heterocyclic oxy group).

Examples of the aliphatic hydrocarbon groups represented by $R_1$, $R_2$, $R_3$ and $R_4$ preferably include an alkyl group (preferably having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably having from 2 to 20, more preferably from 2 to 12, and particularly preferably from2 to 8, carbon atoms, e.g., vinyl, allyl, 2-butenyl, 3-pentenyl), and an alkynyl group (preferably having from 2 to 20, more preferably from 2 to 12, and particularly preferably from 2 to 8, carbon atoms, e.g., propargyl, 3-pentynyl), and more preferably include an alkyl group and an alkenyl group.

The aryl groups represented by $R_1$, $R_2$, $R_3$ and $R_4$ preferably have from 6 to 30, more preferably from 6 to 20, and particularly preferably from 6 to 12, carbon atoms, e.g., phenyl, 4-methylphenyl, 4-methoxyphenyl, 3-trifluoromethylphenyl, pentafluorophenyl, 1-naphthyl, and 2-naphthyl can be exemplified.

The heterocyclic groups represented by $R_1$, $R_2$, $R_3$ and $R_4$ are monocyclic or condensed heterocyclic groups preferably having from 1 to 20, more preferably from 1 to 12, and still more preferably from 2 to 10, carbon atoms. The heterocyclic groups represented by $R_1$, $R_2$, $R_3$ and $R_4$ are preferably aromatic heterocyclic groups containing at least one nitrogen, oxygen, sulfur, or selenium atom. Specific examples of heterocyclic groups represented by $R_1$, $R_2$, $R_3$ and $R_4$ include, e.g., pyrrolidine, piperidine, pyrrole, furan, thiophene, imidazoline, imidazole, benzimidazole, naphthimidazole, thiazolidine, thiazole, benzothiazole, naphthothiazole, isothiazole, oxazoline, oxazole, benzoxazole, naphthoxazole, isoxazole, selenazole, benzoselenazole, naphthoselenazole, pyridine, quinoline, isoquinoline, indole, indolenine, pyrazole, pyrazine, pyrimidine, pyridazine, triazine, indazole, purine, phthalazine, naphthyridine, quinoxaline, quinazoline, cinnoline, pteridine, phenanthridine, pteridine, phenanthroline, and tetraazaindene, preferably furan, thiophene, pyridine, quinoline, pyrazine, pyrimidine, pyridazine, triazine, phthalazine, naphthyridine, quinoxaline, and quinazoline, and more preferably furan, thiophene, pyridine, and quinoline.

The amino groups represented by $R_1$, $R_2$, $R_3$ and $R_4$ preferably have from 0 to 20, more preferably from 1 to 16, and particularly preferably from 1 to 12, carbon atoms, e.g., amino, methylamino, dimethylamino, diethylamino, dibenzylamino, phenylamino and diphenylamino can be exemplified.

The alkoxyl groups represented by $R_1$, $R_2$, $R_3$ and $R_4$ preferably have from 1 to 20, more preferably from 1 to 16, and particularly preferably from 1 to 12, carbon atoms, e.g., methoxy, ethoxy, butoxy, and 2-ethylhexyloxy can be exemplified.

The aryloxy groups represented by $R_1$, $R_2$, $R_3$ and $R_4$ preferably have from 6 to 20, more preferably from 6 to 16, and particularly preferably from 6 to 12, carbon atoms, e.g., phenyloxy, 4-methoxyphenyloxy, 1-naphthyloxy and 2-naphthyloxy can be exemplified.

The heterocyclic oxy groups represented by $R_1$, $R_2$, $R_3$ and $R_4$ preferably have from 1 to 20, more preferably from 2 to 16, and particularly preferably from 2 to 12, carbon atoms, e.g., pyridyloxy and quinolyloxy can be exemplified.

$R_1$, $R_2$, $R_3$ and $R_4$ each may have a substituent. The same groups described as substituents for $Q_1$ can be applied to the substituents for $R_1$, $R_2$, $R_3$ and $R_4$.

$R_1$ and $R_2$ each preferably represents an aliphatic hydrocarbon group, an aryl group, or a heterocyclic group, and more preferably represents an alkyl group, an aryl group, or an aromatic heterocyclic group.

$R_3$ and $R_4$ each preferably represents an aliphatic hydrocarbon group, an aryl group, a heterocyclic group, an alkoxyl group, an aryloxy group, or a heterocyclic oxy group, more preferably represents an alkoxyl group or an aryloxy group, and still more preferably represents an aryloxy group.

Z preferably represents $SO_2R_1$, more preferably represents $SO_2R_5$ (wherein $R_5$ represents an aliphatic hydrocarbon group, an aryl group, or a heterocyclic group), and still more preferably represents $SO_2R_6$ (wherein $R_6$ represents an aliphatic hydrocarbon group, an aryl group, or an aromatic heterocyclic group).

The compound having a partial structure represented by formula (I) is preferably a metal complex having a compound having a partial structure represented by formula (I) as a ligand, and more preferably a metal complex represented by the following formula (K-I).

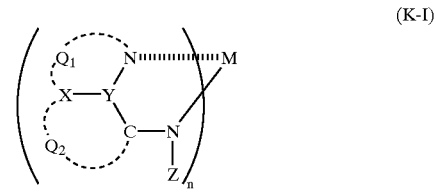

(K-I)

wherein $Q_1$, $Q_2$, X, Y and Z have the same meaning as $Q_1$, $Q_2$, X, Y and Z in formula (I) and preferred ranges of them are also the same.

M represents a metal ion, preferably represents a divalent to tetravalent metal ion, and more preferably a divalent or trivalent metal ion. Specific examples of metal ions represented by M include a beryllium ion, a magnesium ion, a calcium ion, an aluminum ion, a gallium ion, an indium ion, a zirconium ion, a zinc ion, an iron ion, a cobalt ion, a nickel ion, a copper ion, a platinum ion, a palladium ion, a tin ion, a strontium ion, a scandium ion, a silicon ion, a germanium ion, an europium ion, and a terbium ion, preferred examples are a beryllium ion, a magnesium ion, an aluminum ion, a gallium ion, and a zinc ion, more preferred are a beryllium ion, an aluminum ion, and a zinc ion, and still more preferred is a zinc ion. n represents an integer of from 1 to 4 and it varies by the valence of the metal ion. n preferably represents from 2 to 4, and more preferably 2 or 3. When n is from 2 to 4, a plurality of ligands of the metal complex may be the same or different from each other.

The compound represented by formula (K-I) is more preferably represented by formula (K-Ia):

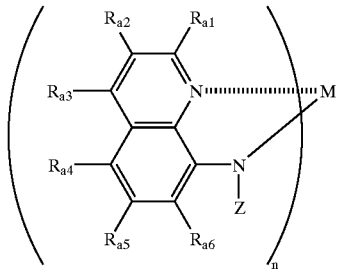

(K-Ia)

wherein Z has the same meaning as Z in formula (I), and preferred range is also the same. M and n have the same meaning as M and n in formula (K-I) and preferred ranges of them are also the same.

$R_{a1}$, $R_{a2}$, $R_{a3}$, $R_{a4}$, $R_{a5}$ and $R_{a6}$ each represents a hydrogen atom or a substituent. As the examples of the substituents, those described as the substituents for the ring formed by $Q_1$ in formula (I) can be applied, and preferred ranges of them are also the same.

The compound represented by formula (K-I) is more preferably represented by formula (K-Ib):

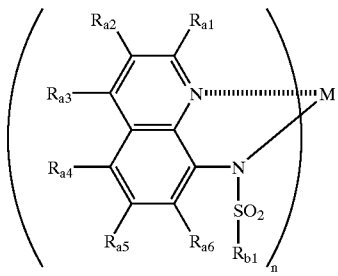

(K-Ib)

wherein M, n, $R_{a1}$, $R_{a2}$, $R_{a3}$, $R_{a4}$, $R_{a5}$ and $R_{a6}$ have the same meaning respectively as those in formula (K-Ia) and respective preferred ranges are also the same; $R_{b1}$ represents an aliphatic hydrocarbon group, an aryl group, or a heterocyclic group, and these aliphatic hydrocarbon group, aryl group, and heterocyclic group have the same meaning as the aliphatic hydrocarbon group, the aryl group, and the heterocyclic group represented by $R_1$, $R_2$, $R_3$ and $R_4$ in formula (I), and respective preferred ranges are also the same; and $R_{b1}$ and $R_{a6}$ may be linked to form a ring.

Of the compounds represented by formula (K-I), when an organic layer is formed by vapor deposition, the compound represented by formula (K-Ic) is preferably used, and when an organic layer is formed by coating, the compound represented by formula (K-Id) is preferably used:

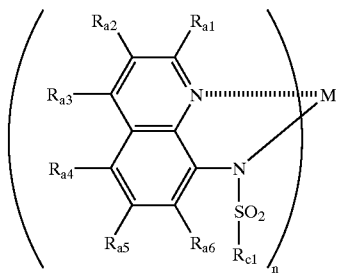

(K-Ic)

wherein M, n, $R_{a1}$, $R_{a2}$, $R_{a3}$, $R_{a4}$, $R_{a5}$ and $R_{a6}$ have the same meaning respectively as those in formula (K-Ia) and respective preferred ranges are also the same; $R_{c1}$ represents an aliphatic hydrocarbon group having 6 or less carbon atoms, an aryl group, or a heterocyclic group, wherein the aryl group and the heterocyclic group have the same meaning respectively as those represented by $R_1$ to $R_4$ in formula (I).

Specific examples of $R_{c1}$ include methyl, ethyl, n-propyl, isopropyl, n-butyl, isobutyl, tert-butyl, n-pentyl, n-hexyl, cyclohexyl, butenyl, phenyl, furyl, thienyl, pyridyl, pyradinyl, pyrimidyl, imidazolyl, thiazolyl, and oxazolyl, preferably methyl, ethyl, phenyl, and thienyl, more preferably methyl, phenyl, and thienyl, and still more preferably phenyl. $R_{c1}$ may have a substituent, and those exemplified as the substituents for $Q_1$ can be applied as the substituent for $R_{c1}$. $R_{c1}$ and $R_{a6}$ may be linked to form a ring;

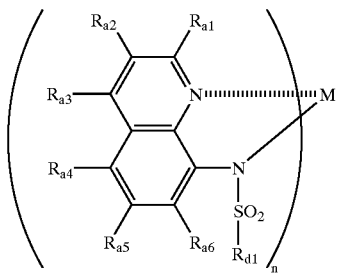

(K-Id)

wherein M, n, $R_{a1}$, $R_{a2}$, $R_{a3}$, $R_{a4}$, $R_{a5}$ and $R_{a6}$ have the same meaning respectively as those in formula (K-Ia) and respective preferred ranges are also the same; $R_{d1}$ represents an aliphatic hydrocarbon group having from 9 to 30 carbon atoms (e.g., n-nonyl, n-decyl, n-dodecyl, n-hexadecyl, n-octadecyl, 3-[2,5-bis(1,1-dimethylpropyl)phenoxy] propyl, 4-[2,5-bis(1,1,3,3-tetramethylbutyl)phenoxy]butyl), an aryl group, or a heterocyclic group. The aryl group and the heterocyclic group have the same meaning respectively as those represented by $R_1$ to $R_4$ in formula (I).

The aliphatic hydrocarbon group, the aryl group, or the heterocyclic group represented by $R_{d1}$ may each have a substituent, e.g., those exemplified as the substituents for $Q_1$ can be applied as the substituent for $R_{a1}$. $R_{d1}$ preferably represents an aliphatic hydrocarbon group having from 9 to 30 carbon atoms including a substituent or an aryl group, more preferably an aliphatic hydrocarbon group having from 9 to 20 carbon atoms or an aryl group, and still more preferably an alkyl group having from 9 to 20 carbon atoms or phenyl group.

The compound represented by formula (K-I) is particularly preferably represented by formula (K-Ie):

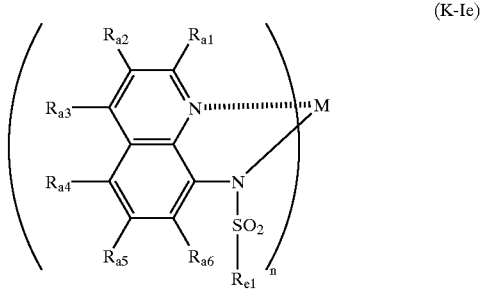

(K-Ie)

wherein M, n, $R_{a1}$, $R_{a2}$, $R_{a3}$, $R_{a4}$, $R_{a5}$ and $R_{a6}$ have the same meaning respectively as those in formula (K-Ia) and respective preferred ranges are also the same; $R_{e1}$ represents an aliphatic hydrocarbon group, an aryl group, or a heterocyclic group each of which has a halogen atom, an alkoxyl group, an aryloxy group or a heterocyclic oxy group as a substituent. The aliphatic hydrocarbon group, the aryl group and the heterocyclic group have the same meaning respectively as those represented by $R_1$ to $R_4$ in formula (I).

The halogen atom is preferably a fluorine atom or a chlorine atom, and more preferably a fluorine atom. The alkoxyl group is preferably an alkoxyl group having 1 to 30, more preferably from 1 to 20, and particularly preferably from 1 to 10, carbon atoms, e.g., methoxy, ethoxy, butoxy, 2-ethylhexyloxy. The aryloxy group is preferably an aryloxy group having from 6 to 30, more preferably from 6 to 20, and particularly preferably from 6 to 12, carbon atoms, e.g., phenyloxy, 1-naphthyloxy, 2-naphthyloxy. The heterocyclic oxy group is preferably a heterocyclic oxy group having from 1 to 30, more preferably from 1 to 12, and particularly preferably from 1 to 10, carbon atoms, and a nitrogen atom, an oxygen atom, a sulfur atom are contained as a hetero atom, e.g., pyridyloxy, quinolyloxy can be exemplified.

The aliphatic hydrocarbon group, the aryl group, or the heterocyclic group represented by $R_{e1}$ may each have a substituent other than a halogen atom, an alkoxyl group, an aryloxy group or a heterocyclic oxy group, and those exemplified as the substituents for $Q_1$ can be applied as the substituent in such a case.

$R_{e1}$ preferably represents an aliphatic hydrocarbon group or an aryl group substituted with an alkoxyl group or an aryloxy group, more preferably an aryl group substituted with an alkoxyl group, and still more preferably a phenyl group substituted with an alkoxyl group.

A more preferred compound according to the present invention is a compound which is negative in "Reverse-Mutation Assay in Bacteria" provided by "Law Concerning the Examination and Regulation of Manufacture, etc., of Chemical Substances", and a compound having a glass transition temperature of not lower than 130° C. is preferred in view of the durability of a luminescence element.

The compound represented by formula (I), (K-I), (K-Ia), (K-Ib), (K-Ic), (K-Id) or (K-Ie) may be a low molecular weight compound, may be a high molecular weight compound in which the residue represented by formula (I), (K-I), (K-Ia), (K-Ib), (K-Ic), (K-Id) or (K-Ie) is connected to the polymer main chain, or may be a high molecular weight compound whose main chain has the skeleton of formula (I), (K-I), (K-Ia), (K-Ib), (K-Ic), (K-Id) or (K-Ie). The high molecular weight compound may be a homopolymer or a copolymer with other monomers.

Further, formula (I), (K-I), (K-Ia), (K-Ib), (K-Ic), (K-Id) or (K-Ie) is conveniently represented as an extreme structural formula but the compound may be a tautomer.

Specific examples of the compounds having a partial structure represented by formula (I) according to the present invention are shown below, but the present invention is not limited thereto.

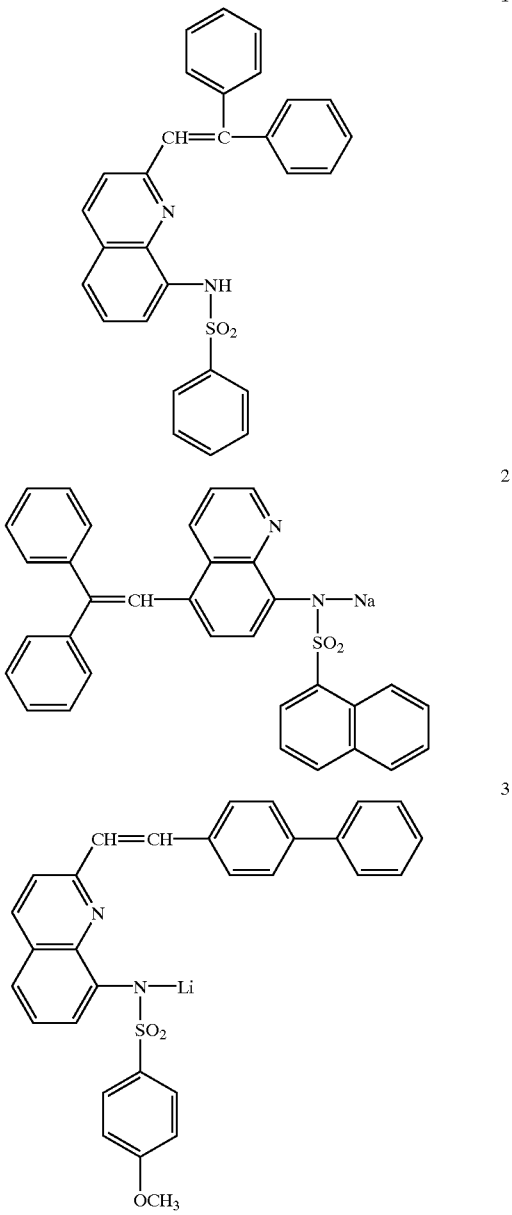

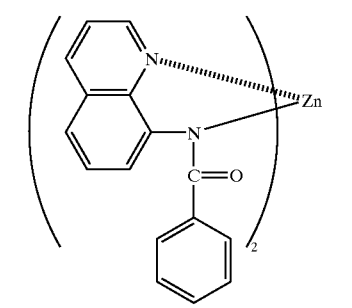
4
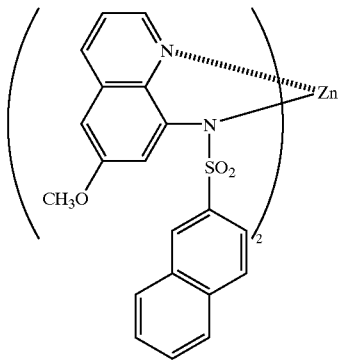
8
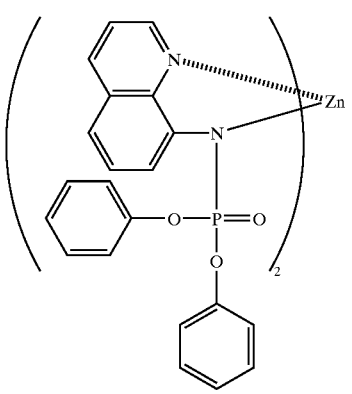
5
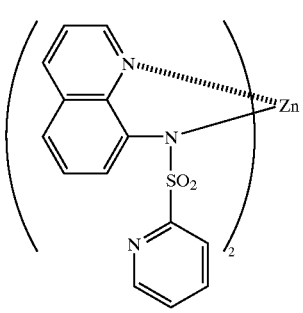
9
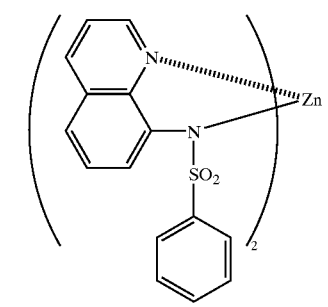
6
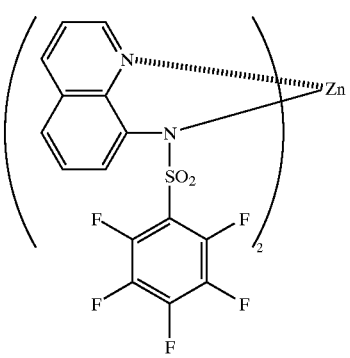
10
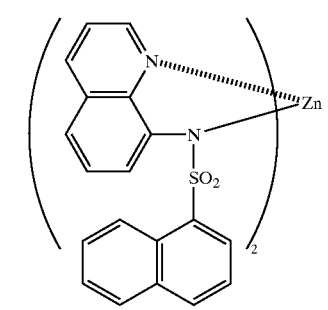
7
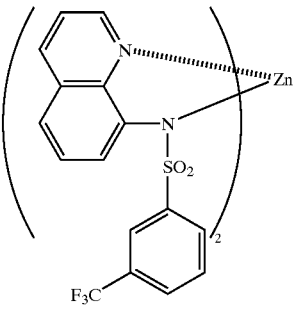
11

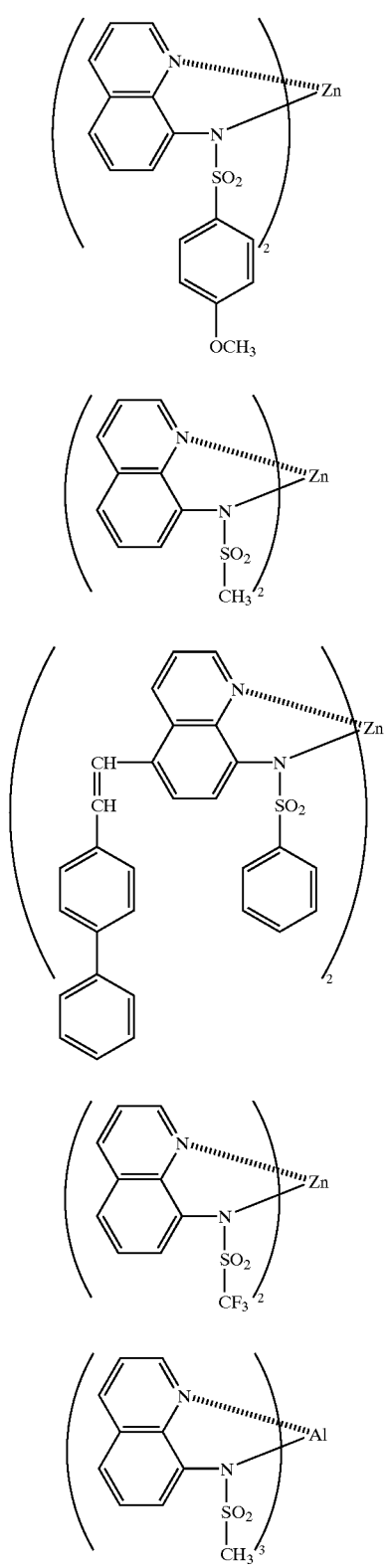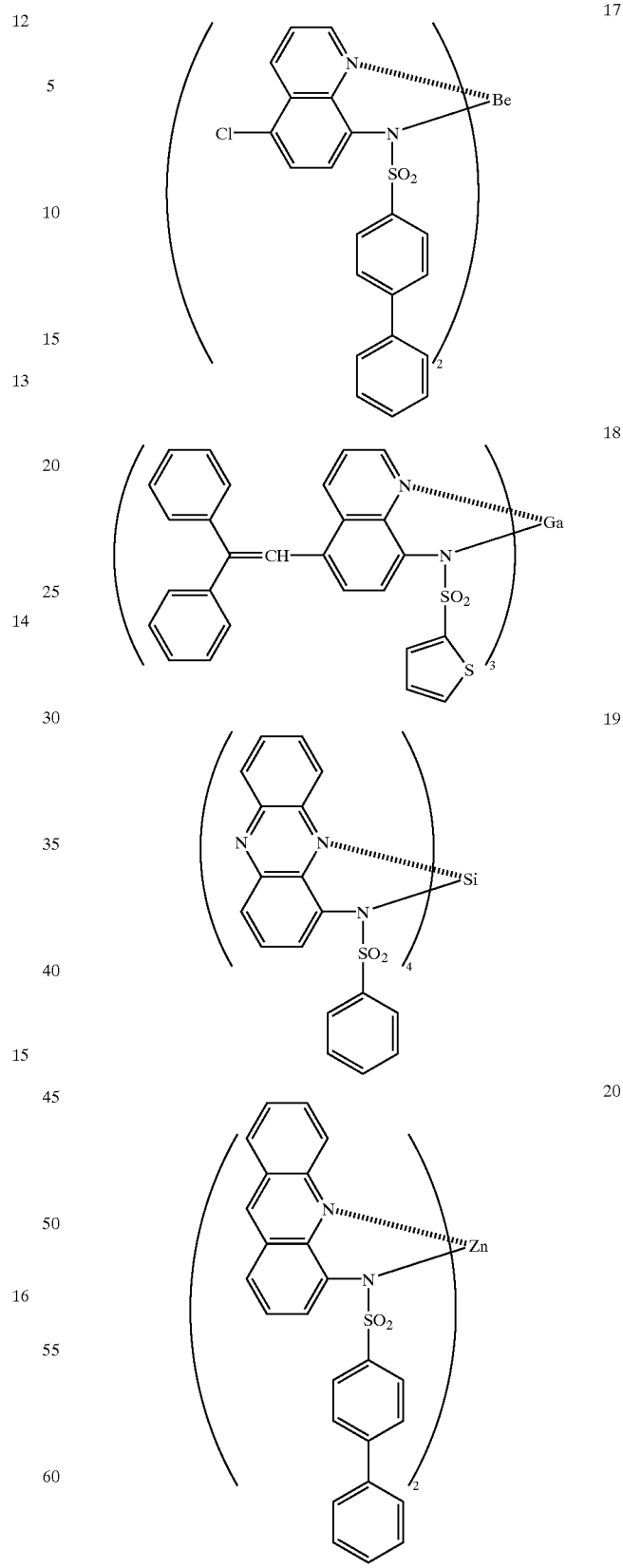

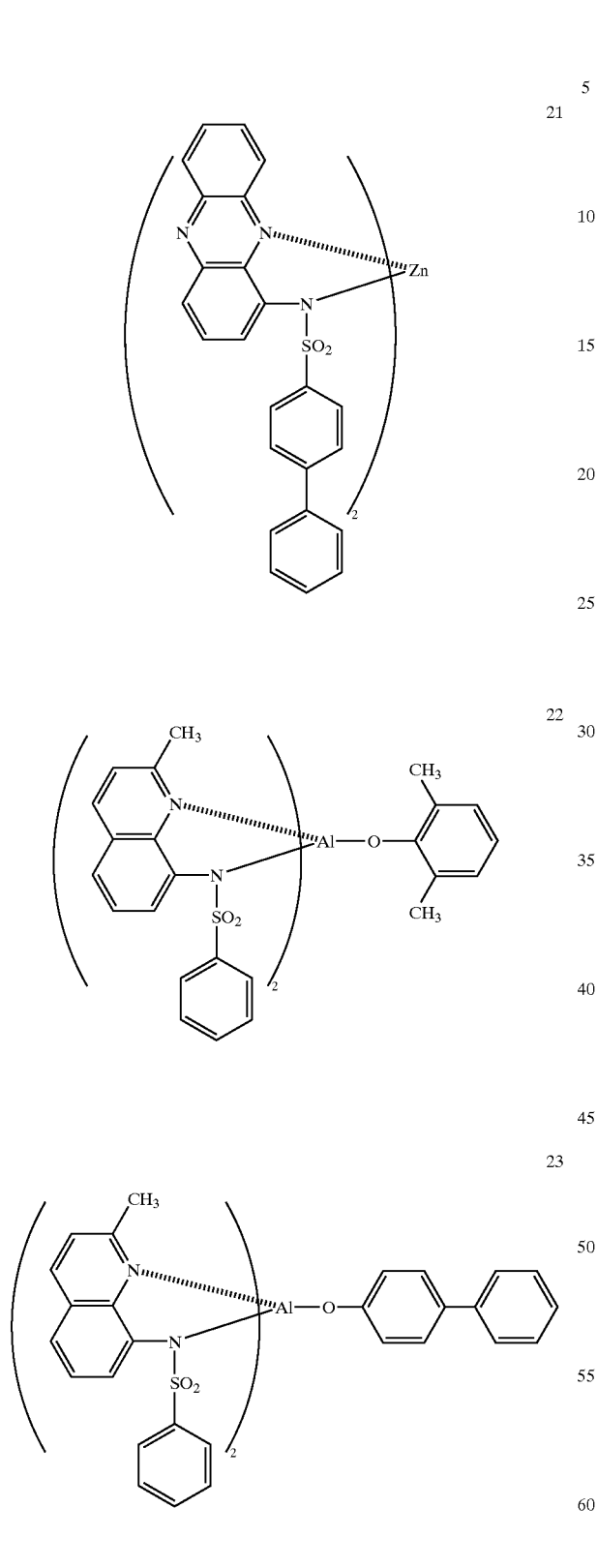
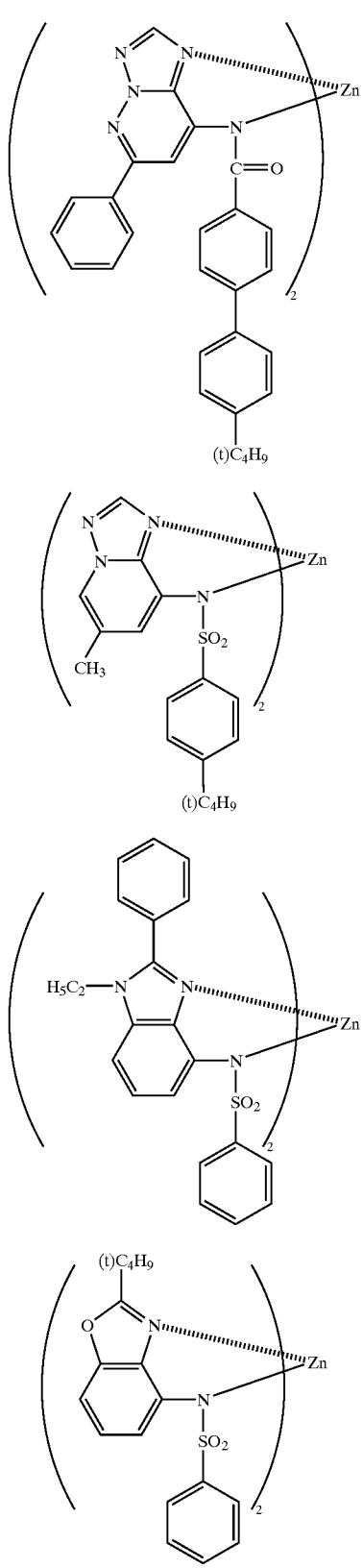

28
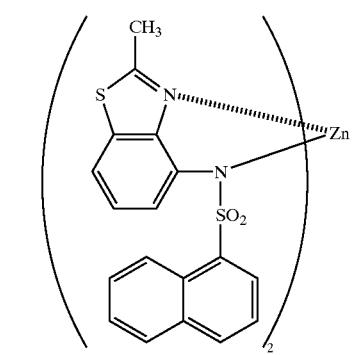
29
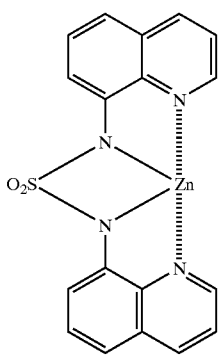
30
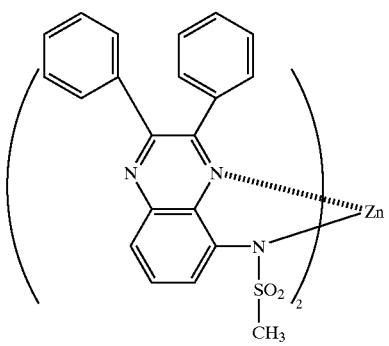
31
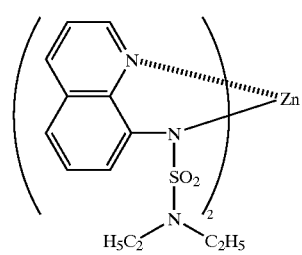
32
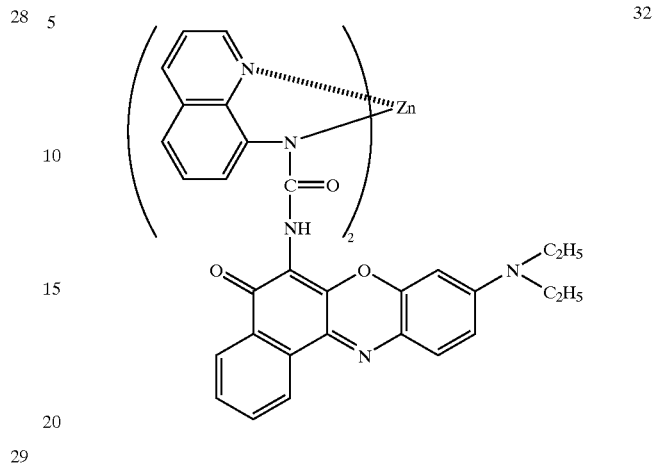
33
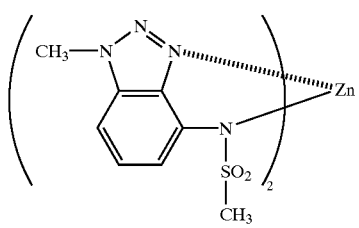
34
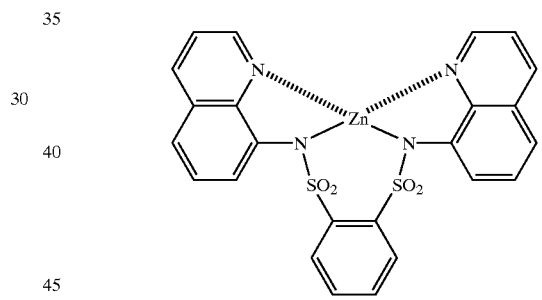
35
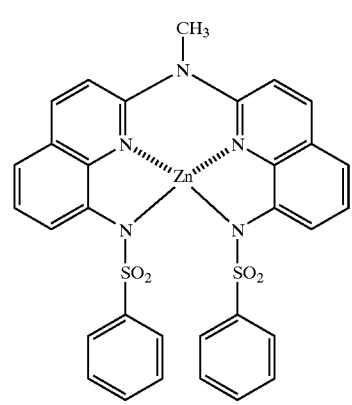

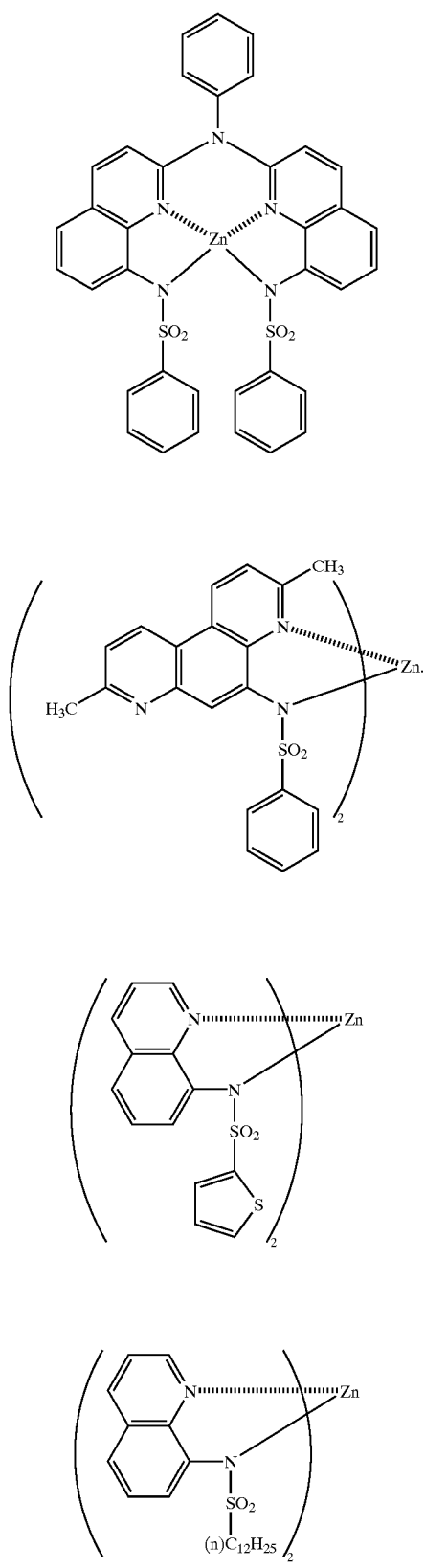
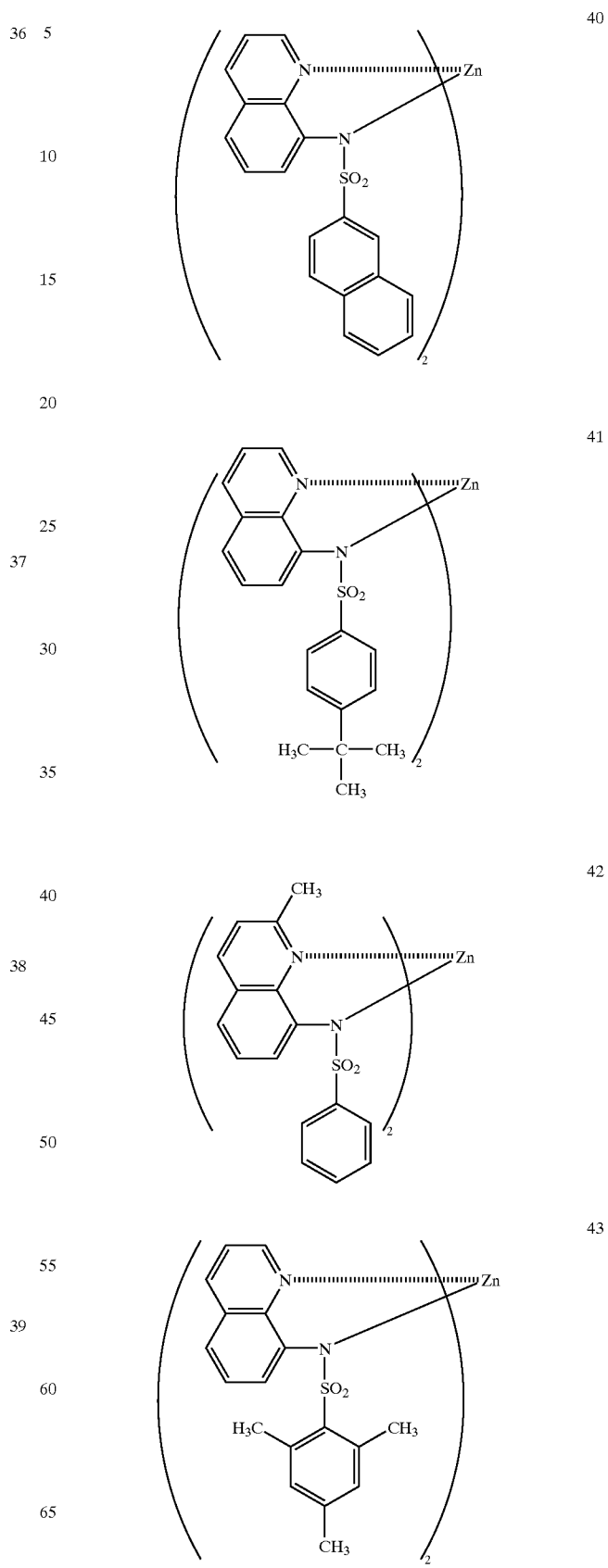

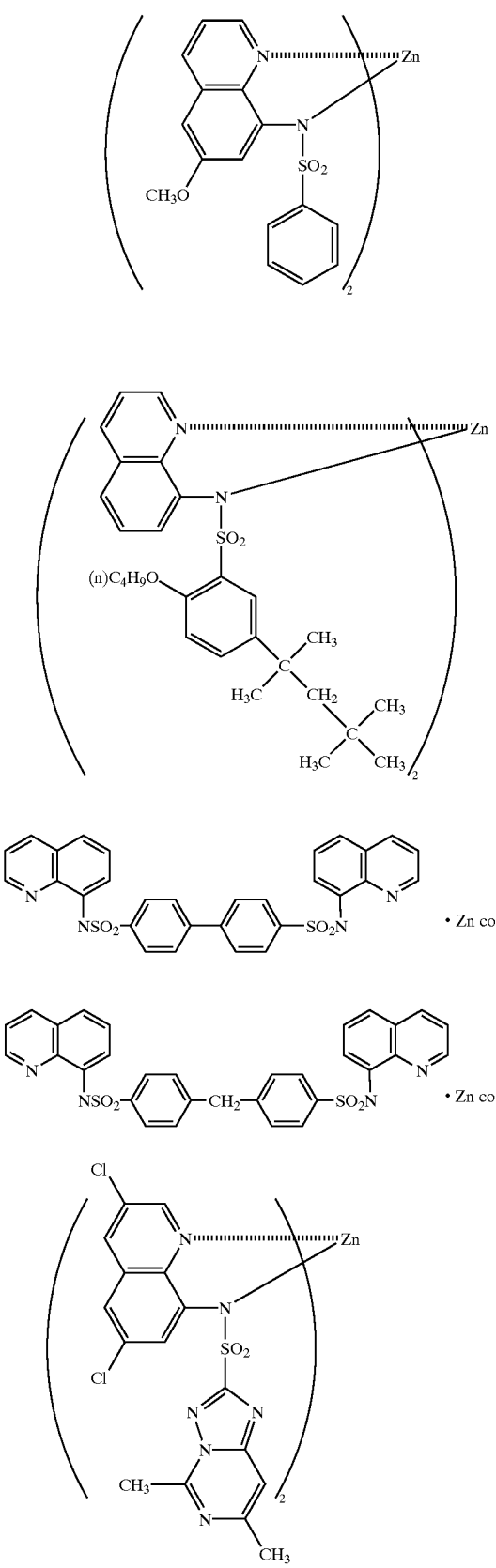
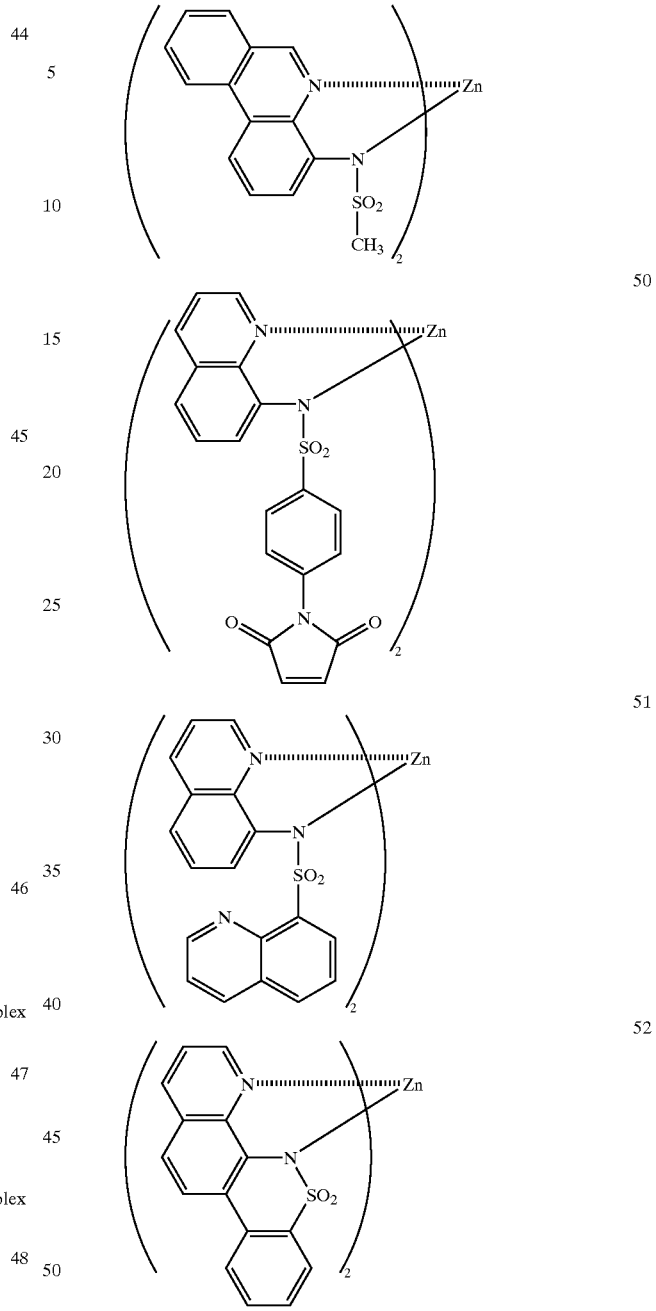

Further, the above exemplified compounds may have other ligands.

Metal salts for use as a starting material in the synthesis of the metal complex according to the present invention are not particularly restricted, for example, halide (fluoride, chloride, bromide, iodide, etc.), sulfate, carboxylate (acetate, etc.), phosphonate, sulfonate, hydroxide, etc., are suitably used, and nitrate, hydrochloride, sulfate, acetate are preferably used.

The molar ratio of a ligand to a metal salt for use in the synthesis of a metal complex is arbitrarily selected according to the complex to be synthesized. In general, a ligand is used from 0.1 to 10 time mol, preferably from 0.5 to 8 time mol, and still more preferably from 0.5 to 6 time mol, of a metal ion.

Further, a base can be used in the synthesis of a metal complex, e.g., various kinds of inorganic or organic bases. For example, a metal hydroxide (e.g., sodium hydroxide, potassium hydroxide), a metal carbonate (e.g., sodium carbonate, potassium carbonate), a metal hydrogencarbonate (e.g., sodium hydrogencarbonate, potassium hydrogencarbonate), and an organic base (e.g., triethylamine, sodium alkoxide) are preferably used.

The amount of a base is not particularly restricted but is preferably from 0.01 to 30 equivalent, more preferably from 1 to 10 equivalent, based on the ligand.

Solvents may be used in the synthesis of a metal complex. Solvents are not particularly limited, for example, water, alcohols (e.g., methanol, ethanol, 2-propanol), esters (e.g., ethyl acetate), ethers (e.g., diethyl ether, tetrahydrofuran, 1,4-dioxane), amides (e.g., dimethylformamide, dimethylacetamide), nitriles (e.g., acetonitrile), ketones (e.g., acetone, cyclohexanone), hydrocarbons (e.g., hexane, benzene, toluene), halogenated hydrocarbons (e.g., dichloromethane, chloroform, 1,2-dichloroethane), carboxylic acids (e.g., acetic acid) can be used. These solvents may be used as mixtures. Preferred solvents are alcohols, ethers and ketones, more preferred are alcohols, and particularly preferred are methanol, ethanol and 2-propanol.

The reaction temperature in synthesis of a metal complex is not particularly restricted but is preferably from 10 to 150° C., more preferably from 10 to 100° C., and most preferably from 10 to 80° C.

Synthesis of the compound according to the present invention is explained below with specific examples.

SYNTHESIS EXAMPLE 1

Synthesis of Exemplified Compound 6

1-1 Synthesis of 8-Benzenesulfonylaminoquinoline

8-Aminoquinoline (25.0 g) (0.173 mol) was dissolved in 100 ml of dimethylacetamide, and 26.5 ml (0.19 mol) of triethylamine and 2 g (0.0164 mol) of 4-dimethylaminopyridine were added to the above solution at 0° C. under the nitrogen atmosphere. Then, 33.6 g (0.190 mol) of benzenesulfonyl chloride was dropwise added to the reaction solution while maintaining the reaction temperature at 0° C. or less. After completion of the dropwise addition, the temperature was gradually raised and the reaction was continued for 1 hour at 10° C. Next, the reaction solution was poured into water and solids precipitated were filtered out and recrystallized with 2-propanol, thereby 43.7 g of the objective compound was obtained. Yield: 89%.

1-2 Synthesis of Exemplified Compound 6

After 1.42 g (4.99 mmol) of the above-synthesized 8-benzenesulfonylaminoquinoline was dissolved in 15 ml of methanol, 1.03 ml (5.02 mmol) of a 28% sodium methoxide solution was added thereto. While stirring the mixture at room temperature, a solution of 10 ml of methanol containing 550 mg (2.51 mmol) of zinc acetate dihydrate was dropwise added thereto. The mixed solution was stirred for 8 hours, then solids precipitated were filtered out and washed with methanol, thereby 1.32 g of Compound 6 was obtained as pale yellowish green solids. Yield: 83%. Melting point: 305–306° C. or more.

SYNTHESIS EXAMPLE 2

Synthesis of Exemplified Compound 7

2-1 Synthesis of 8-(1-Naphthalene sulfonylamino)quinoline

8-Aminoquinoline (23.8 g) (0.165 mol) was dissolved in 100 ml of dimethylacetamide, and 26.5 ml (0.19 mol) of triethylamine and 2 g (0.0164 mol) of 4-dimethylaminopyridine were added to the above solution at 0° C. under the nitrogen atmosphere. Then, 34.5 g (0.152 mol) of 1-naphthalenesulfonyl chloride was dropwise added to the reaction solution while maintaining the reaction temperature at 0° C. or less. After completion of the dropwise addition, the temperature was gradually raised and the reaction was continued for 1 hour at 10° C. Next, the reaction solution was poured into water and solids precipitated were filtered out and recrystallized with acetonitrile, thereby 43.0 g of the objective compound was obtained. Yield: 85%.

2-2 Synthesis of Exemplified Compound 7

After 3.34 g (0.01 mol) of the above-synthesized 8-(1-naphthalenesulfonylamino)quinoline was dissolved in 30 ml of methanol, 2.10 ml (0. 01mol) of a 28% sodium methoxide solution was added thereto. While stirring the mixture at room temperature, a solution of 15 ml of methanol containing 1.10 g (0.005 mol) of zinc acetate dehydrate was dropwise added thereto. The mixed solution was stirred for 5 hours, then solids precipitated were filtered out and washed with methanol, thereby 3.01 g of Compound 7 was obtained as pale yellowish green solids. Yield: 90%. Melting point: 290° C. or more.

SYNTHESIS EXAMPLE 3

Synthesis of Exemplified Compound 10

3-1 Synthesis of 8-(Pentaflulorobenzenesulfonylamino)quinoline

8-Aminoquinoline (13.5 g) (0.094 mol) was dissolved in 100 ml of dimethylacetamide. Then, 25.0 g (0.094 mol) of pentafluorobenzenesulfonyl chloride was dropwise added thereto slowly at 0° C. under the nitrogen atmosphere. After completion of the dropwise addition, the temperature was gradually raised and the reaction was continued for 8 hours at room temperature. The reaction solution was then poured into a chilled dilute aqueous hydrochloric acid, the solids precipitated were filtered out and recrystallized with acetonitrile, thereby 18.3 g of the objective compound was obtained. Yield: 52%.

3-2 Synthesis of Exemplified Compound 10

After 3.74 g (0.01 mol) of the above-synthesized 8-(pentafluorobenzenesulfonylamino)quinoline was dissolved in 30 ml of methanol, 2.05 ml (0.01 mol) of a 28% sodium methoxide solution was added thereto. While stirring the mixture at room temperature, a solution of 15 ml of methanol containing 1.10 g (0.005 mol) of zinc acetate dehydrate was dropwise added thereto. The mixed solution was stirred for 5 hours at room temperature, then the solids precipitated were filtered out and washed with methanol, thereby 3.72 g of Compound 10 was obtained as pale yellowish green solids. Yield: 92%. Melting point: 303° C.

SYNTHESIS EXAMPLE 4

Synthesis of Exemplified Compound 11

4-1 Synthesis of 8-[3-(Trifluoromethyl)benzenesulfonyl-amino]quinoline

8-Aminoquinoline (14.4 g) (0.100 mol) was dissolved in 150 ml of acetonitrile, and 8.0 g (0.10 mol) of pyridine was added to the above solution at 0° C. under the nitrogen atmosphere. Then, 25.0 g (0.102 mol) of 3-(trifluoromethyl) benzenesulfonyl chloride was dropwise added thereto slowly while maintaining the reaction temperature at 5° C. or less. After completion of the dropwise addition, the temperature was gradually raised and the reaction was continued for 1 hour at room temperature. The reaction solution was then poured into a chilled dilute aqueous hydrochloric acid. After extraction with ethyl acetate, the organic phase was washed with water and dried over anhydrous magnesium sulfate. The solvent was distilled off under reduced pressure. The reaction product was purified by silica gel column chromatography (developing solvent: chloroform) and recrystallized with chloroform/n-hexane, thereby 31.8 g of the objective compound was obtained. Yield: 90%.

4-2 Synthesis of Exemplified Compound 11

After 3.52 g (0.01 mol) of the above-synthesized 8-[3-(trifluoromethyl)benzenesulfonylamino]quinoline was dissolved in 30 ml of methanol, 2.05 ml (0.01 mol) of a 28% sodium methoxide solution was added thereto. While stirring the mixture at room temperature, a solution of 15 ml of methanol containing 1.10 g (0.005 mol) of zinc acetate dihydrate was dropwise added thereto. The mixed solution was stirred for 10 hours at room temperature, then the solids precipitated were filtered out and washed with methanol, thereby 3.75 g of Compound 11 was obtained as pale yellowish green solids. Yield: 98%. Melting point: 242° C.

SYNTHESIS EXAMPLE 5

Synthesis of Exemplified Compound 12

5-1 Synthesis of 8-(4-Methoxybenzenesulfonylamino) quinoline

8-Aminoquinoline (25.0 g) (0.173 mol) was dissolved in 200 ml of dimethylacetamide, and 26.5 ml (0.19 mol) of triethylamine and 2 g (0.0164 mol) of 4-dimethylaminopyridine were added to the above solution at 0° C. under the nitrogen atmosphere. Then, 39.4 g (0.191 mol) of 4-methoxybenzenesulfonyl chloride was dropwise added thereto slowly while maintaining the reaction temperature at 5° C. or less. After completion of the dropwise addition, the temperature was gradually raised and the reaction was continued for 4 hours at room temperature. The reaction solution was then poured into a dilute aqueous hydrochloric acid. After extraction with chloroform, the organic phase was washed with water and dried over anhydrous magnesium sulfate. The solvent was distilled off under reduced pressure. The reaction product was purified by silica gel column chromatography (developing solvent: chloroform→chloroform/methanol=10/1 (by volume ratio)) and recrystallized with chloroform/n-hexane, thereby 25.3 g of the objective compound was obtained. Yield: 47%.

5-2 Synthesis of Exemplified Compound 12

After 3.14 g (0.01 mol) of the above-synthesized 8-(4-methoxybenzenesulfonylamino)quinoline was dissolved in 30 ml of methanol, 2.10 ml (0.01 mol) of a 28% sodium methoxide solution was added thereto. While stirring the mixture at room temperature, a solution of 15 ml of methanol containing 1.10 g (0.005 mol) of zinc acetate dihydrate was dropwise added thereto. After the mixed solution was stirred and refluxed with heating for 5 hours, the solids precipitated were filtered out and washed with methanol, thereby 3.10 g of Compound 12 was obtained as pale yellowish green solids. Yield: 93%. Melting point: 273–275° C.

SYNTHESIS EXAMPLE 6

Synthesis of Exemplified Compound 13

6-1 Synthesis of 8-(Methanesulfonylamino)quinoline

8-Aminoquinoline (26.0 g) (0.180 mol) was dissolved in 100 ml of acetonitrile, and 15.8 g (0.20 mol) of pyridine was added to the above solution at 0° C. under the nitrogen atmosphere. Then, 21.1 g (0.185 mol) of methanesulfonyl chloride was dropwise added thereto slowly while maintaining the reaction temperature at 10° C. or less. After completion of the dropwise addition, the temperature was gradually raised and the reaction was continued for 6 hours at room temperature. The reaction solution was then poured into a dilute aqueous hydrochloric acid. The pH value was adjusted to 5 with an aqueous potassium carbonate solution. The solids precipitated were filtered out, washed with water, and the solids obtained were recrystallized with acetonitrile, thereby 31.0 g of the objective compound was obtained. Yield: 78%.

6-2 Synthesis of Exemplified Compound 13

After 5.02 g (0.023 mol) of the above-synthesized 8-(methanesulfonylamino)quinoline was dissolved in 60 ml of methanol, 4.36 g (0.023 mol) of a 28% sodium methoxide solution was addedt hereto. While stirring the mixture at room temperature, a solution of 56 ml of methanol containing 2.48 g (0.0113 mol) of zinc acetate dihydrate was dropwise added thereto. After the mixed solution was stirred and refluxed with heating for 2 hours, the solids precipitated were filtered out and washed with methanol, thereby 5.73 g of Compound 13 was obtained as pale yellowish green solids. Yield: 99%. Melting point: 300° C. or more.

SYNTHESIS EXAMPLE 7

Synthesis of Exemplified Compound 15

7-1 Synthesis of 8-(Trifluoromethanesulfonylamino) quinoline

8-Aminoquinoline (12.8 g) (0.0886 mol) was dissolved in 100 ml of acetonitrile. Then, 25.0 g (0.0886 mol) of trifluoromethanesulfonic anhydride was dropwise added thereto slowly under the nitrogen atmosphere while maintaining the reaction temperature at 10° C. or less. After completion of the dropwise addition, the temperature was gradually raised and the reaction was continued for 5 hours at room temperature. The reaction solution was then poured into ice water. After the reaction solution was washed with saturated brine, the organic phase was dried over anhydrous magnesium sulfate. The solvent was distilled off under reduced pressure, and the solids obtained were recrystallized with acetonitrile, thereby 18.9 g of the objective compound was obtained. Yield: 77%.

7-2 Synthesis of Exemplified Compound 15

After 2.76 g (0.01 mol) of the above-synthesized 8-(trifluoromethanesulfonylamino)quinoline was dissolved in 15 ml of methanol, 2.05 g (0.01 mol) of a 28% sodium methoxide solution was added thereto. While stirring the mixture at room temperature, a solution of 15 ml of methanol containing 1.108 g (0.005 mol) of zinc acetate dihydrate was dropwise added thereto. The mixed solution was stirred for 6 hours at room temperature, then the solids precipitated were filtered out and washed with methanol, thereby 2.80 g of Compound 15 was obtained as white solids. Yield: 91%. Melting point: 288–289° C.

SYNTHESIS EXAMPLE 8

Synthesis of Exemplified Compound 38

8-1 Synthesis of 8-(2-Thiophenesulfonylamino)quinoline

8-Aminoquinoline (17.3 g) (0.120 mol) was dissolved in 100 ml of dimethylacetamide. Then, a solution of 50 ml of dimethylacetamide containing 23.0 g (0.1261 mol) of 2-thiophenesulfonyl chloride was dropwise added thereto slowly under the nitrogen atmosphere while maintaining the reaction temperature at 10° C. or less. After completion of the dropwise addition, the temperature was gradually raised and the reaction was continued for 8 hours at room temperature. The reaction solution was then poured into a chilled dilute aqueous hydrochloric acid. The solids precipitated were filtered out, washed with water, and the solids obtained were recrystallized with acetonitrile, thereby 9.9 g of the objective compound was obtained. Yield: 28%.

8-2 Synthesis of Exemplified Compound 38

After 2.90 g (0.01 mol) of the above-synthesized 8-(2-thiophenesulfonylamino)quinoline was dissolved in 30 ml of methanol, 2.05 ml (0.01 mol) of a 28% sodium methoxide solution was added thereto. While stirring the mixture at room temperature, a solution of 15 ml of methanol containing 1.10 g (0.005 mol) of zinc acetate dihydrate was dropwise added thereto. The mixed solution was reacted for 10 hours at room temperature, then the solids precipitated were filtered out and washed with methanol, thereby 3.00 g of Compound 38 was obtained as pale yellowish green solids. Yield: 93%. Melting point: 331° C.

SYNTHESIS EXAMPLE 9

Synthesis of Exemplified Compound 39

9-1 Synthesis of 8-(Dodecanesulfonylamino)quinoline

8-Aminoquinoline (17.3 g) (0.120 mol) was dissolved in 100 ml of acetonitrile, and 9.89 g (0.125 mol) of pyridine was added to the above solution under the nitrogen atmosphere. Then, a solution of 50 ml of acetonitrile containing 35.4 g (0.132 mol) of dodecanesulfonyl chloride was dropwise added thereto slowly while maintaining the reaction temperature at 10° C. or less. After completion of the dropwise addition, the temperature was gradually raised and the reaction was continued for 2 hours at room temperature. The reaction solution was then poured into water. The solids precipitated were filtered out, washed with water, and the solids obtained were recrystallized with acetonitrile, thereby 38.3 g of the objective compound was obtained. Yield: 85%.

9-2 Synthesis of Exemplified Compound 39

After 3.76 g (0.01 mol) of the above-synthesized 8-(dodecanesulfonylamino)quinoline was dissolved in 30 ml of methanol, 2.05 ml (0.01 mol) of a 28% sodium methoxide solution was added thereto. While stirring the mixture at room temperature, a solution of 15 ml of methanol containing 1.10 g (0.005 mol) of zinc acetate dihydrate was dropwise added thereto. The mixed solution was reacted for 10 hours at room temperature, then the solids precipitated were filtered out and washed with methanol, thereby 1.70 g of Compound 39 was obtained as pale yellowish green solids. Yield: 42%. Melting point: 122–125° C.

SYNTHESIS EXAMPLE 10

Synthesis of Exemplified Compound 40

10-1 Synthesis of 8-(2-Naphthalenesulfonylamino)quinoline

8-Aminoquinoline (28.8 g) (0.20 mol) was dissolved in 250 ml of dimethylacetamide, and 30.5 ml (0.219 mol) of triethylamine and 2 g (0.0164 mol) of 4-dimethylaminopyridine were added to the above solution at 0° C. under the nitrogen atmosphere. Then, 50.0 g (0.220 mol) of 2-naphthalenesulfonyl chloride was dropwise added thereto slowly while maintaining the reaction temperature at 5° C. or less. After completion of the dropwise addition, the temperature was gradually raised and the reaction was continued for 1 hour at room temperature. The reaction solution was then poured into a chilled dilute aqueous hydrochloric acid. The solids precipitated were filtered out and the solids obtained were recrystallized with acetonitrile, thereby 47.2 g of the objective compound was obtained. Yield: 71%.

10-2 Synthesis of Exemplified Compound 40

After 3.34 g (0.01 mol) of the above-synthesized 8-(2-naphthalenesulfonylamino)quinoline was dissolved in 30 ml of methanol, 2.10 ml (0.01 mol) of a 28% sodium methoxide solution was added thereto. While stirring the mixture at room temperature, a solution of 15 ml of methanol containing 1.10 g (0.005 mol) of zinc acetate dihydrate was dropwise added thereto. After the mixed solution was stirred for 8 hours, the solids precipitated were filtered out and washed with methanol, thereby 3.23 g of Compound 40 was obtained as pale yellowish green solids. Yield: 88%. Melting point: 301–303° C.

SYNTHESIS EXAMPLE 11

Synthesis of Exemplified Compound 41

11-1 Synthesis of 8-(4-tert-Butylbenzenesulfonylamino) quinoline

8-Aminoquinoline (50.8 g) (0.352 mol) was dissolved in 300 ml of acetonitrile, and 29.0 ml (0.359 mol) of pyridine was added to the above solution at 0° C. under the nitrogen atmosphere. Then, a solution of 250 ml of acetonitrile containing 67.9 g (0.356 mol) of 4-tert-butylbenzenesulfonyl chloride was dropwise added thereto slowly while maintaining the reaction temperature at 5° C. or less. After completion of the dropwise addition, the temperature was gradually raised and the reaction was continued for 5 hours at room temperature. The reaction solution was then poured into a chilled dilute aqueous hydrochloric acid. The solids precipitated were filtered out, washed with water, and the solids obtained were recrystallized with acetonitrile, thereby 96.7 g of the objective compound was obtained. Yield: 92%.

11-2 Synthesis of Exemplified Compound 41

After 53.7 g (0.18 mol) of the above-synthesized 8-(4-tert-butylbenzenesulfonylamino) quinoline was dissolved in 600 ml of methanol, 34.7 g (0.18 mol) of a 28% sodium methoxide solution was added thereto. While stirring the mixture at room temperature, a solution of 450 ml of methanol containing 19.8 g (0.09 mol) of zinc acetate dihydrate was dropwise added thereto. After the mixed solution was stirred and refluxed with heating for 3 hours, the solids precipitated were filtered out and washed with methanol, thereby 58.9 g of Compound 41 was obtained as pale yellowish green solids. Yield: 99%. Melting point: 300° C. or more.

SYNTHESIS EXAMPLE 12

Synthesis of Exemplified Compound 42

12-1 Synthesis of 8-Benzeneslfonylamino-2-methylquinoline

8-Amino-2-methylquinoline (10.5 g) (0.067 mol) was dissolved in 100 ml of acetonitrile, and 6.0 ml (0.074 mol) of pyridine was added to the above solution at 0° C. under the nitrogen atmosphere. Then, a solution of 20 ml of acetonitrile containing 11.9 g (0.067 mol) of benzenesulfonyl chloride was dropwise added thereto slowly while maintaining the reaction temperature at 5° C. or less. After completion of the dropwise addition, the temperature was gradually raised and the reaction was continued for 3 hours at room temperature. The reaction solution was then poured into a chilled dilute aqueous hydrochloric acid. The solids precipitated were filtered out, washed with water, and the solids obtained were recrystallized with ethanol, thereby 15.1 g of the objective compound was obtained. Yield: 76%.

12-2 Synthesis of Exemplified Compound 42

After 2.98 g (0.01 mol) of the above-synthesized 8-benzenesulfonylamino-2-methylquinoline was dissolved in 50 ml of methanol, 1.93 g (0.01 mol) of a 28% sodium methoxide solution was added thereto. While stirring the mixture at room temperature, a solution of 25 ml of methanol containing 1.10 g (0.005 mol) of zinc acetate dihydrate was dropwise added thereto. After the mixed solution was stirred and refluxed with heating for 3 hours, the solids precipitated were filtered out and washed with methanol, thereby 3.20 g of Compound 42 was obtained as pale yellowish green solids. Yield: 97%. Melting point: 300° C. or more.

SYNTHESIS EXAMPLE 13

Synthesis of Exemplified Compound 43

13-1 Synthesis of 8-(2,4,6-Trimethylbenzenesulfonylamino)-quinoline

8-Aminoquinoline (15.3 g) (0.106 mol) was dissolved in 100 ml of acetonitrile, and 8.7 ml (0.108 mol) of pyridine was added to the above solution at 0° C. under the nitrogen atmosphere. Then, a solution of 100 ml of acetonitrile containing 23.5 g (0.107 mol) of 2,4,6-trimethylbenzenesulfonyl chloride was dropwise added thereto slowly while maintaining the reaction temperature at 5° C. or less. After completion of the dropwise addition, the temperature was gradually raised and the reaction was continued for 5 hours at room temperature. The reaction solution was then poured into a chilled dilute aqueous hydrochloric acid. The solids precipitated were filtered out, washed with water, and the solids obtained were recrystallized with acetonitrile, thereby 30.3 g of the objective compound was obtained. Yield: 88%.

13-2 Synthesis of Exemplified Compound 43

After 13.1 g (0.04 mol) of the above-synthesized 8-(2,4,6-trimethylbenzenesulfonylamino)quinoline was dissolved in 200 ml of methanol, 7.72 g (0.04 mol) of a 28% sodium methoxide solution was added thereto. While stirring the mixture at room temperature, a solution of 90 ml of methanol containing 4.38 g (0.02 mol) of zinc acetate dihydrate was dropwise added thereto. After the mixed solution was stirred and refluxed with heating for 2 hours, the solids precipitated were filtered out and washed with methanol, thereby 14.0 g of Compound 43 was obtained as pale yellowish green solids. Yield: 98%. Melting point: 300° C. or more.

SYNTHESIS EXAMPLE 14

Synthesis of Exemplified Compound 44

14-1 Synthesis of 8-Benzenesulfonylamino-6-methoxyquinoline

8-Amino-6-methoxyquinoline (0.90 g) (5.17 mmol) was dissolved in 10 ml of acetonitrile, and 0.5 ml (6.18 mmol) of pyridine was added to the above solution at 0° C. under the nitrogen atmosphere. Then, 0.91 g (5.17 mmol) of benzenesulfonyl chloride was dropwise added thereto slowly while maintaining the reaction temperature at 5° C. or less. After completion of the dropwise addition, the temperature was gradually raised and the reaction was continued for 2 hours at room temperature. The reaction solution was then poured into a chilled dilute aqueous hydrochloric acid. The solids precipitated were filtered out, washed with water, and the solids obtained were recrystallized with acetonitrile, thereby 1.25 g of the objective compound was obtained. Yield: 80%.

14-2 Synthesis of Exemplified Compound 44

After 1.00 g (3.18 mol) of the above-synthesized 8-benzenesulfonylamino-6-methoxyquinoline was dissolved in 15 ml of methanol, 0.614 g (3.18 mmol) of a 28% sodium methoxide solution was added thereto. While stirring the mixture at room temperature, a solution of 5 ml of methanol containing 0.349 g (1.59 mmol) of zinc acetate dihydrate was dropwise added thereto. After the mixed solution was stirred and refluxed with heating for 3 hours, the solids precipitated were filtered out and washed with methanol, thereby 1.1 g of Compound 44 was obtained as pale yellowish green solids. Yield: 99%. Melting point: 300° C. or more.

SYNTHESIS EXAMPLE 15

Synthesis of Exemplified Compound 45

15-1 Synthesis of 8-[2-Butoxy-5-(1,1,3,3-tetramethylpentyl)-benzpnesulfonylamino]quinoline 8-Aminoquinoline (11.5 g) (0.080 mol) was dissolved in 150 ml of acetonitrile, and 6.6 ml (0.082 mol) of pyridine was added to the above solution at 0° C. under the nitrogen atmosphere. Then, a solution of 30 ml of acetonitrile containing 29.5 g (0.082 mol) of 2-butoxy-5-(1,1,3,3-tetramethylpentyl)-benzenesulfonyl chloride was dropwise added thereto slowly while maintaining the reaction temperature at 5° C. or less. After completion of the dropwise addition, the temperature was gradually raised and the reaction was continued for 5 hours at room temperature. The reaction solution was then poured into a chilled dilute aqueous hydrochloric acid. The solids precipitated were filtered out, washed with water, and the solids obtained were recrystallized with ethanol, thereby 31.6 g of the objective compound was obtained. Yield: 84%.

15-2 Synthesis of Exemplified Compound 45

After 51.6 g (0.11 mol) of the above-synthesized 8-[2-butoxy-5-(1,1,3,3-tetramethylpentyl)benzenesulfonylamino]quinoline was dissolved in 400 ml of methanol, 21.2 g (0.11 mol) of a 28% sodium methoxide solution was added thereto. While stirring the mixture at room temperature, a solution of 250 ml of methanol containing 12.1 g (0.055 mol) of zinc acetate dihydrate was dropwise added thereto. After the mixed solution was stirred and refluxed with heating for 4.5 hours, the solids precipitated were filtered out and washed with methanol, thereby 51.4 g of Compound 45 was obtained as pale yellowish green solids. Yield: 93%. Melting point: 168–170° C.

The luminescence element according to the present invention comprises a pair of electrodes of the anode and the cathode having formed therebetween a luminescence layer or a plurality of organic compound thin film layers comprising a luminescence layer, and may comprise a hole-injecting layer, a hole-transporting layer, an electron-injecting layer, an electron-transporting layer, a protecting layer, etc., in addition to a luminescence layer. Each of these layers may have different functions. Various materials can be used to form each layer.

The anode is to supply holes to a hole-injecting layer, a hole-transporting layer, a luminescence layer, etc., andmetals, alloys, metal oxides, electrically conductive compounds, or mixtures of these can be used therefor, and materials having a work function of 4 eV or more are preferably used. Specific examples of such materials include electrically conductive metal oxides such as a tin oxide, a zinc oxide, an indium oxide, an indium tin oxide (ITO), etc., metals such as gold, silver, chromium, nickel, etc., mixtures or laminates of these metals with electrically conductive metal oxides, inorganic electrically conductive materials such as copper iodide, copper sulfide, etc., organic electrically conductive materials such as polyaniline, polythiophene, polypyrrole, etc., and laminates of these materials with ITO. Electrically conductive metal oxides are preferably used, and ITO is particularly preferably used in view of productivity, high conductivity and transparency. The film thickness of the anode can be selected arbitrarily according to materials used but is generally preferably from 10 nm to 5 μm, more preferably from 50 nm to 1 μm, and still more preferably from 100 nm to 500 nm.

The anode generally comprises lamination formed on a soda-lime glass, non-alkali glass or transparent resin substrate. When a glass substrate is used, non-alkali glass is preferably used for lessening elution of ions from the glass. Further, when soda-lime glass is used, it is preferred to provide a barrier coat such as silica. The thickness of the substrate is not particularly limited so long as it can sufficiently stand the physical strength. When glass is used, the thickness is generally 0.2 mm or more, preferably 0.7 mm or more.

Various processes are used in the manufacture of the anode according to the materials to be used. In the case of using ITO, for example, thin films are formed by an electron beam process, a sputtering process, a resistance heating deposition process, a chemical reaction process (a sol-gel process), or the process of coating the dispersion of an indium tin oxide.

It is possible to reduce the driving voltage or increase the luminescence efficacy of the element by the process such as washing of the anode. In the case of using ITO, for example, UV-ozone processing and plasma processing are effective.

The cathode is to supply electrons to an electron-injecting layer, an electron-transporting layer, a luminescence layer, etc., and the cathode is selected taking into consideration the adhesion with the adjacent electron-injecting layer, electron-transporting layer, luminescence layer, etc., ionization potential and stability. As materials of the cathode, metals, alloys, metal oxides, electrically conductive compounds, or mixtures of these materials can be used. Specific examples include alkali metals (e.g., Li, Na, K) or fluorides of them, alkaline earth metals (e.g., Mg, Ca) or fluorides of them, gold, silver, lead, aluminum, sodium-potassium alloys or mixed metals of them, lithium-aluminum alloys or mixed metals of them, magnesium-silver alloys or mixed metals of them, and rare earth metals such as indium, ytterbium, etc., preferably materials having a work function of 4 eV or less, and more preferably aluminum, lithium-aluminum alloys or mixed metals of them, and magnesium-silver alloys or mixed metals of them. The film thickness of the cathode can be selected arbitrarily according to materials used but is generally preferably from 10 nm to 5 μm, more preferably from 50 nm to 1 μm, and still more preferably from 100 nm to 1 μm.

Processes such as an electron beam process, a sputtering process, a resistance heating deposition process, and a coating process are used in the manufacture of the cathode, and a single metal can be vapor deposited or two or more components can be deposited at the same time. Further, a plurality of metals can be deposited at the same time to form an alloy electrode, alternatively a previously prepared alloy can be deposited.

It is preferred that the sheet resistance of the anode and the cathode be low, preferably several hundred Ω/□ or less.

The luminescence layer may be made of any material so long as, when electric field is applied, the luminescence layer formed does not prevent holes from being injected from the anode, the hole-injecting layer and the hole-transporting layer, electrons from being injected from the cathode, the electron-injecting layer and the electron-transporting layer, and offers the functions of transferring the electric charge injected and recombining the electrons and holes to effect emission. Preferably the luminescence layer contains the compound according to the present invention but luminescent materials other than the compound according to the present invention can also be used, and as such materials, e.g., benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyrralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes represented by metal complexes of 8-quinolinol derivatives and rare earth metal complexes, and polymer compounds such as polythiophene, polyphenylene, and polyphenylenevinylene are exemplified. The film thickness of the luminescence layer is not particularly restricted but it is generally preferably from 1 nm to 5 μm, more preferably from 5 nm to 1 μm, and still more preferably from 10 nm to 500 nm.

The luminescence layer can be formed by any process, e.g., a resistance heating deposition process, an electron beam process, a sputtering process, a molecular lamination process, a coating process (a spin coating process, a cast coating process, a dip coating process), an LB process, or ink jet process is used, preferably a resistance heating deposition process and a coating process.

Preferably, the layer containing the compound of the present invention further contains at least one kind of other fluorescent compound. The fluorescent compound to be used may be either organic or inorganic, and preferably is an organic fluorescent compound. Examples of such a fluorescent compound include the above-described luminescence materials and the known fluorescent compounds. The amount of a fluorescent compound is not particularly restricted but is preferably from 0.001 to 20% by weight, more preferably from 0.01 to 10% by weight, particularly preferably from 0.1 to 1% by weight, based on the compound of the present invention.

Materials of the hole-injecting layer and the hole-transporting layer are sufficient if they have any of the functions of injecting holes from the anode, transporting holes, and barriering off the electrons injected from the cathode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine deriva-tives, arylamine derivatives, amino-substituted chalcone derivatives, styrylanthracene derivatives, fluorenone deriva-tives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, aniline-based copolymers, and electrically conductive high molecular weight oligomers such as tihophene oligomers and polythiophene oligomers. The film thickness of the hole-injecting layer and the hole-transporting layer is not particularly limited but it is generally preferably from 1 nm to 5 µm, more preferably from 5 nm to 1 µm, and still more preferably from 10 nm to 500 nm. The hole-injecting layer and the hole-transporting layer may be single layer structure comprising one or two or more of the above materials, or may be multilayer structure comprising a plurality of layers of the same composition or different compositions.

The hole-injecting layer and the hole-transporting layer are formed by a vacuum deposition process, an LB process, an ink jet process, or the process of dissolving or dispersing the above-described hole-injecting and transporting agent in a solvent and coating (a spin coating process, a cast coating process, a dip coating process). In the case of a coating process, a hole-injecting and transporting agent can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, etc.

Materials of the electron-injecting layer and the electron-transporting layer are sufficient if they have any of the functions of injecting electrons from the cathode, transporting electrons, and barriering off the holes injected from the anode. Specific examples of the materials include not only the compounds according to the present invention but also triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidene methane derivatives, distyrylpyrazine derivatives, heterocyclic tetracarboxylic anhydride such as naphthaleneperylene, phthalocyanine derivatives, and various metal complexes represented by metal complexes of 8-quinolinol derivatives and metal complexes having a ligand such as metal phthalocyanine, benzoxazole or benzothiazole. The film thickness of the electron-injecting layer and the electron-transporting layer is not particularly restricted but it is generally preferably from 1 nm to 5 µm, more preferably from 5 nm to 1 µm, still more preferably from 10 nm to 500 nm, and particularly preferably from 10 nm to 80 nm. The electron-injecting layer and the electron-transporting layer may be single layer structure comprising one or two or more of the above materials, or may be multilayer structure comprising a plurality of layers of the same composition or different compositions.

The electron-injecting layer and the electron-transporting layer are formed by a vacuum deposition process, an LB process, an ink jet process, or the process of dissolving or dispersing the above-described electron-injecting and transporting agent in a solvent and coating (a spin coating process, a cast coating process, a dip coating process). In the case a coating process, an electron-injecting and transporting agent can be dissolved or dispersed with a resin component. As the resin components, those exemplified in the hole-injecting and transporting layers can be applied.

Materials of the protective layer are sufficient if they have the function of preventing substances which accelerates the deterioration of the element, such as water or oxygen, from entering the element. Specific examples of the materials include metals, e.g., In, Sn, Pb, Au, Cu, Ag, Al, Ti, Ni, etc., metal oxides, e.g., MgO, SiO, $SiO_2$, $Al_2O_3$, GeO, NiO, CaO, BaO, $Fe_2O_3$, $Y_2O_3$, $TiO_2$, etc., metal fluorides, e.g., $MgF_2$, LiF, $AlF_3$, $CaF_2$, etc., polyethylene, polypropylene, polymethylmethacrylate, polyimide, polyurea, polytetrafluoroethylene, polychlorotrifluoroethylene, polydichlorodifluoroethylene, copolymers of chlorotrifluoro-ethylene and dichlorodifluoroethylene, copolymers obtained by copolymerizing monomer mixtures containing tetrafluoroethylene and at least one comonomer, fluorine-containing copolymers having cyclic structure at the main chain of the copolymer, water-absorbing substances having a water absorption coefficient of 1% or more, and moisture-proof materials having a water absorption coefficient of 0.1% or less.

The forming process of the protective layer is also not particularly restricted and, e.g., a vacuum deposition process, a sputtering process, a reactive sputtering process, an MBE (molecular beam epitaxy) process, a cluster ion beam process, an ion-plating process, a plasma polymerization process (a high frequency exciting ion-plating process), a plasma CVD process, a laser CVD process, a heat CVD process, a gas source CVD process, an ink jet process, or a coating process can be applied.

As the constitution of the luminescence element according to the present invention, it is preferred that the organic compound thin film layers comprise at least three layers of a hole-transporting material, a luminescence layer and an electron-transporting layer, and the electron-transporting layer contains at least one material for a luminescence element of the present invention. In this case, the luminescence layer preferably comprises a single compound from the viewpoint of the simplification of the manufacturing method of the luminescence element, the reproducibility improvement of the characteristics of the element, and the inhibition of the fluctuation of the luminescence element with the lapse of time.

EXAMPLES

The present invention is specifically described below with referring to examples, but the present invention is not limited thereto.

Example 1

On a washed glass substrate with ITO electrodes were vacuum deposited in order of phthalocyanine in a film thickness of 5 nm, bis[N-(1-naphthyl)-N-phenyl]benzidine in a film thickness of 40 nm, and the compound shown in Table 1 below in a film thickness of 60 nm (from $8\times10^{-4}$ to $1\times10^{-5}$ Torr). A mask which had been subjected to patterning (a mask having a luminescence area of 5 mm×5 mm) was set thereon, and magnesium/silver in a ratio of 10/1 was co-deposited in a thickness of 250 nm, then silver was deposited in a thickness of 300 nm (from $8\times10^{-6}$ to $1\times10^{-5}$ Torr). Thus, a luminescence element was prepared.

Direct current constant voltage was applied to the luminescence element with making ITO the anode and Mg/Ag the cathode to effect light emission using source measuring unit model 2400 manufactured by Toyo Technica Co., Ltd. The luminance was measured by using luminance meter BM-8 manufactured by Topcon Co., Ltd., and the luminescence wavelength was measured using spectrum analyzer PMA-11 manufactured by Hamamatsu Photonics Co., Ltd. The produced element was allowed to stand at 60° C., 20% RH for 3 hours, then effected light emission and the relative luminance uminance after aging expressed by a relative value taking the minance immediately after production of the element as 100 riving voltage: 10 V)) and the generation of dark spot on the minescent surface were evaluated. The results obtained are own in Table 1 below.

invention is used requires low minimum driving voltage and exhibits high luminance emission. Further, the reduction of luminance and the generation of dark spot after storage at high temperature are less, which shows that the luminescence element according to the present invention is excellent in durability.

TABLE 1

| Sample No. | Compound | Luminescence Wavelength λmax (nm) | Maximum Luminance (cd/m$^2$) | Minimum Driving Voltage (V) | Relative Luminance after Aging | Generation of Dark spot | Remarks |
|---|---|---|---|---|---|---|---|
| 1 | Comparative Compound A | 520 | 7,800 | 6 | 54 | Present | Comparison |
| 2 | Comparative Compound B | 541 | 8,300 | 7 | 38 | Present | Comparison |
| 3 | Compound 6 | 526 | 17,800 | 4 | 91 | Absent | Invention |
| 4 | Compound 7 | 548 | 15,900 | 4 | 88 | Absent | Invention |
| 5 | Compound 13 | 525 | 10,920 | 4 | 91 | Absent | Invention |
| 6 | Compound 30 | 552 | 9,900 | 4 | 82 | Absent | Invention |

Comparative Compound A (Al9)

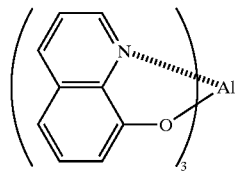

Example 2

On an ITO substrate having been subjected to etching and washing in the same manner as in Example 1 were deposited copper phthalocyanine in a thickness of 5 nm of and TPD [N,N'-bis(3-methylphenyl)-N,N'-diphenylbenzidine] in a thickness of 40 nm, and then red luminescence material (Nile Red) and the compound shown in Table 2were co-deposited at depositing rate of 0.04 Å/sec and 4 Å/sec, respectively, in a film thickness of 60 nm. Subsequently, Al/Li in a ratio of 100/2 were co-deposited in a film thickness of 200 nm. Thus, a luminescence element was prepared. Luminance and chromaticity at driving voltage of 8 V and 15 V were measured. The results obtained are shown in Table 2 below.

TABLE 2

| Sample No. | Compound | Maximum Luminance (cd/m$^2$) Driving at 8 V | Maximum Luminance (cd/m$^2$) Driving at 15 V | CIE Chromaticity Coordinates (x, y) Driving at 8 V | CIE Chromaticity Coordinates (x, y) Driving at 15 V | Remarks |
|---|---|---|---|---|---|---|
| 1 | Comparative Compound A | 890 | 2,800 | (0.66, 0.33) | (0.55, 0.41) | Comparison |
| 2 | Compound 6 | 6,200 | 12,600 | (0.66, 0.33) | (0.65, 0.34) | Invention |
| 3 | Compound 7 | 6,610 | 13,500 | (0.66, 0.33) | (0.65, 0.35) | Invention |
| 4 | Compound 13 | 4,800 | 9,860 | (0.66, 0.33) | (0.64, 0.35) | Invention |
| 5 | Compound 30 | 4,230 | 8,840 | (0.66, 0.33) | (0.64, 0.34) | Invention |

Comparative Compound A was the same as used in Example 1.

Comparative Compound B (Znq)

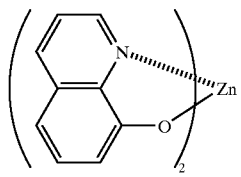

Red Luminescence Material (Nile Red)

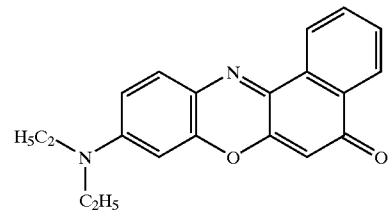

From the results shown in Table 1, it can be seen that the element in which the compound according to the present It is apparent from the results shown in Table 2 that the elements in which the compound according to the present invention is used exhibits high luminance emission even when the system is doped with a fluorescent compound. Further, the red color purity of the element in which Alq is used as a host compound is reduced when driving voltage is increased, on the other hand the color purity of the elements in which the compound according to the present invention is used as a host compound hardly changes, thus it can be seen that high luminance emission with high color purity can be obtained.

Example 3

Poly(N-vinylcarbazole) (40 mg), 0.5 mg of 1,1,4,4-tetraphenylbutadiene, and 12 mg of the compound shown in Table 3 below were dissolved in 3 ml of 1,2-dichloroethane and spin-coated on a washed ITO substrate. The film thickness of the organic thin film layer formed was about 110 nm. A mask which had been subjected to patterning (a mask having a luminescent area of 5 mm×5 mm) was set on the organic thin film layer, and magnesium/silver in the ratio of 10/1 was co-deposited in a thickness of 50 nm in a vapor deposition apparatus, then silver was deposited in a thickness of 150 nm. Thus, a luminescence element was prepared. Evaluation of the thus-formed element was performed in the same manner as in Example 1. The results obtained are shown in Table 3 below.

voltage as compared with the elements using the comparative compounds even in a coating system where luminance is generally low. In the element in which Comparative Compound C (PBD) is used, generation of dark spot is conspicuous, while the elements according to the present invention exhibit good planar light emission. Further, in the element in which Comparative Compound A (Alq) is used, luminescence of Alq is mainly observed and the blue color purity is reduced, therefore this element does not effectively function as a host material for blue color luminescence. On the contrary, the elements in which the compound according to the present invention is used exhibit high blue color purity and can function as excellent host materials for blue color luminescence.

Example 4

On a washed glass substrate with ITO electrodes were vacuum deposited in order of copper phthalocyanine in a film thickness of 5 nm, bis[N-(1-naphthyl)-N-phenyl]benzidine in a film thickness of 40 nm, the material for a luminescence layer shown in Table 4 below in a film thickness of 20 nm, the material for an electron-transporting layer shown in Table 4 below in a film thickness of 60 nm, and LiF in a film thickness of 1 nm (from $8\times10^{-6}$ to $1\times10^{-5}$ Torr). A mask which had been subjected to patterning (a mask having a luminescence area of 4 mm×5 mm) was set

TABLE 3

| Sample No. | Compound | Minimum Driving Voltage (V) | Maximum Luminance (cd/m$^2$) | CIE Chromaticity Coordinates (x, y) | Generation of Dark Spot | Remarks |
| --- | --- | --- | --- | --- | --- | --- |
| 1 | Comparative Compound A | 12 | 620 | (0.32, 0.52) | Absent | Comparison |
| 2 | Comparative Compound C | 14 | 31 | (0.17, 0.19) | Present | Comparison |
| 3 | Compound 4 | 9 | 1,890 | (0.17, 0.19) | Absent | Invention |
| 4 | Compound 6 | 8 | 2,450 | (0.17, 0.19) | Absent | Invention |
| 5 | Compound 7 | 8 | 2,200 | (0.17, 0.20) | Absent | Invention |
| 6 | Compound 13 | 8 | 2,060 | (0.18, 0.21) | Absent | Invention |

Comparative Compound A was the same as used in Example 1.

Comparative Compound C (PBD)

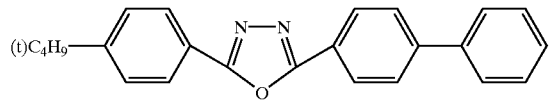

As is apparent from the results in Table 3, the elements in which the compound according to the present invention is used can exhibit high luminance emission with low driving thereon, and Al/Li in a ratio of 100/1 was co-deposited in a thickness of 250 nm, then Al was deposited in a thickness of 300 nm (from $8\times10^{-6}$ to $1\times10^{-5}$ Torr). Thus, a luminescence element was produced.

Each of the obtained elements was evaluated in the same manner as in Example 1. The results obtained are shown in Table 4 below.

TABLE 4

| Sample No. | Luminescence Material | Electron-transporting Material | Luminescence wavelength $\lambda_{max}$ (nm) | Maximum Luminance (cd/m$^2$) | CIE Chromaticity Coordinates (x, y) | Remarks |
| --- | --- | --- | --- | --- | --- | --- |
| 1 | Blue Luminescence Material B | Comparative Compound A[a)] | 463 | 2410 | 0.16, 0.17 | Comparison |
| 2 | Green Luminescence Material G | Comparative Compound A[a)] | 536 | 2820 | 0.35, 0.58 | |

TABLE 4-continued

| Sample No. | Luminescence Material | Electron-transporting Material | Luminescence wavelength $\lambda_{max}$ (nm) | Maximum Luminance (cd/m$^2$) | CIE Chromaticity Coordinates (x, y) | Remarks |
|---|---|---|---|---|---|---|
| 3 | Red Luminescence Material R | Comparative Compound A[a] | 648 | 1150 | 0.63, 0.35 | Δ |
| 4 | Blue Luminescence Material B | Compound 6 | 463 | 3140 | 0.16, 0.16 | Invention |
| 5 | Blue Luminescence Material B | Compound 11 | 461 | 3200 | 0.16, 0.15 | Δ |
| 6 | Blue Luminescence Material B | Compound 15 | 460 | 2970 | 0.15, 0.15 | Δ |
| 7 | Green Luminescence Material G | Compound 6 | 539 | 8710 | 0.36, 0.59 | Δ |
| 8 | Green Luminescence Material G | Compound 13 | 537 | 6330 | 0.36, 0.58 | Δ |
| 9 | Green Luminescence Material G | Compound 38 | 538 | 7220 | 0.35, 0.58 | Δ |
| 10 | Red Luminescence Material R | Compound 6 | 648 | 4840 | 0.64, 0.34 | Δ |
| 11 | Red Luminescence Material R | Compound 7 | 646 | 4160 | 0.64, 0.35 | Δ |
| 12 | Red Luminescence Material R | Compound 12 | 648 | 5290 | 0.64, 0.34 | Δ |
| 13 | Red Luminescence Material R | Compound 13 | 646 | 3970 | 0.64, 0.34 | Δ |
| 14 | Red Luminescence Material R | Compound 40 | 647 | 4030 | 0.64, 0.35 | Δ |
| 15 | Red Luminescence Material R | Compound 42 | 648 | 4760 | 0.64, 0.34 | Δ |
| 16 | Red Luminescence Material R | Compound 43 | 647 | 3880 | 0.64, 0.35 | Δ |
| 17 | Red Luminescence Material R | Compound 44 | 648 | 5320 | 0.64, 0.35 | Δ |

[a] Comparative Compound A was the same as used in Example 1
[b] Chromaticity Coordinates Driving at 10 V Blue Luminescence Material B

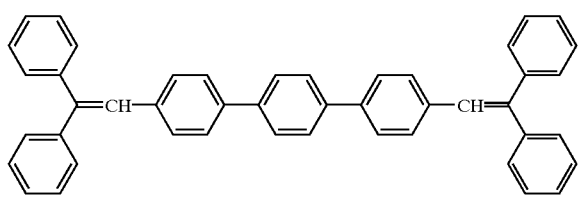

Green Luminescence Material G

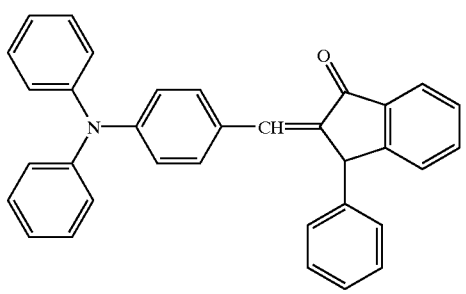

Red Luminescence Material R

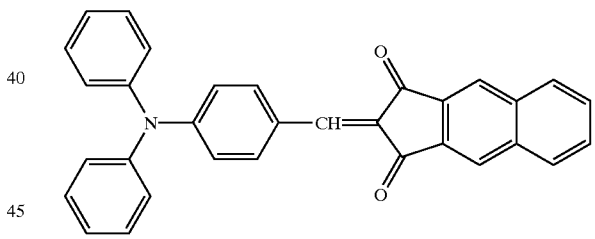

From the results shown in Table 4, it can be seen that when the compound according to the present invention is used, even the non-doped type element having a luminescence layer consisting of one luminescence compound is capable of high luminance emission, and is excellent in color purity.

Example 5

Poly(N-vinylcarbazole) (40 mg) was dissolved in 3 ml of 1,2-dichloroethane and spin-coated on a washed ITO substrate in a film thickness of 60 nm. Then, 3 ml of a methanol solution containing Compound 45 according to the present invention (12 mg), a red luminescence material RA (2 mg), and poly(butyral) (40 mg) was spin coated in a film thickness of 40 nm. A mask which had been subjected to patterning (a mask having a luminescent area of 4 mm×5 mm) was set on the organic thin film, and magnesium/silver in the ratio of 10/1 was co-deposited in a thickness of 50 nm in a vapor deposition apparatus, then silver was deposited in a thickness of 150 nm. Thus, a luminescence element was produced. Voltage (10 V) was applied to the element with making ITO the anode and Mg/Ag the cathode. Luminance and chromaticity were 1,280 cd/m² and (0.64, 0.34) respectively, which shows that the coating type element also exhibits high luminance and excellent red color purity.
Red Luminescence Material RA

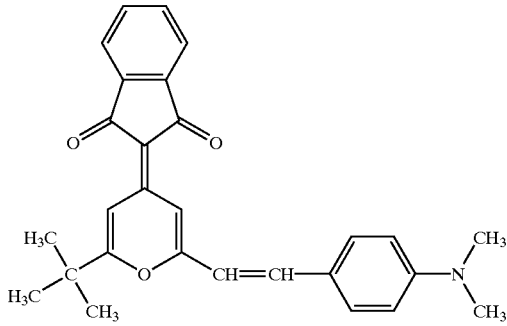

Example 6

Compounds 6, 13 and 45 according to the present invention were subjected to "Reverse-Mutation Assay in Bacteria" provided by "Law Concerning the Examination and Regulation of Manufacture, etc., of Chemical Substances" (commonly called "Ames test"). As a result, all of these compounds were negative and the safety of the materials was confirmed.

Example 7

The glass transition temperatures of the compounds according to the present invention were measured using SSCE 5200H and RDC220 manufactured by Seiko Instruments Co., Ltd. As a result, the glass transition temperature of Compound 6 was 137° C. and that of Compound 38 was 139° C. The glass transition temperatures of organic materials largely affect the durability of organic EL elements. It is known that in general the higher the glass transition temperature, the better is the durability. Consequently, it can be seen from the above test that the compound according to the present invention is excellent in heat resistance and durability.

An organic EL element capable of light emission of high luminance and having good durability can be obtained according to the present invention. In particular, excellent luminous characteristics can be obtained even in a coating system where luminance is generally low, therefore, an element can be produced advantageously from the viewpoint of the production cost. Further, an organic EL element which shows little variation in chromaticity due to difference of driving voltage can be obtained according to the present invention.

While the invention has been described in detail and with reference to specific examples thereof, it will be apparent to one skilled in the art that various changes and modifications can be made therein without departing from the spirit and scope thereof.

What is claimed is:

1. A luminescence element comprising a pair of electrodes having formed therebetween a plurality of organic compound thin film layers comprising an electron-transporting layer, wherein the electron-transporting layer comprises a compound represented by the formula (K-Ie):

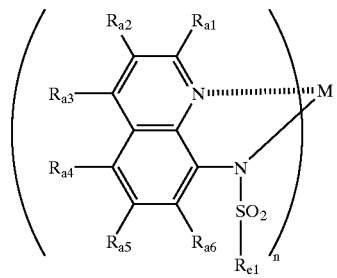

wherein $R_{e1}$ represents an aliphatic hydrocarbon group, an aryl group, or a heterocyclic group and each of which groups is substituted with at least one group selected from the group consisting of a halogen atom and an alkoxy group; M represents a metal ion; n represents an integer of from 1 to 4; and $R_{a1}$, $R_{a2}$, $R_{a3}$, $R_{a4}$, $R_{a5}$ and $R_{a6}$ each represents a hydrogen atom or a substitutent.

2. The luminescence element of claim 1, wherein the electron-transporting layer is a layer formed by coating.

3. The luminescence element of claim 1, wherein the electron-trasnporting layer is a layer comprising a compound represented by the formula (K-Ie):

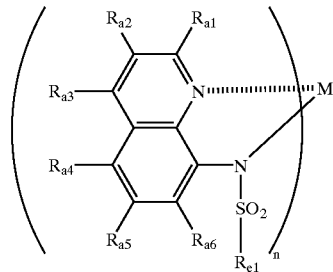

dispersed in a polymer.

4. The luminescence element of claim 1, wherein the layer containing said compound further contains at least one kind of other fluorescent compound.

5. The luminescence element of claim 1, wherein the electron-transporting layer has a film thickness of from 1 to 80 nm.

6. A material for a luminescence element, which is a compound represented by the following formula (K-Ie):

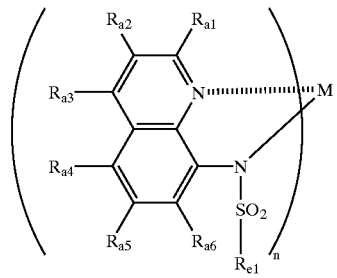

wherein $R_{e1}$ represents an aryl group or a heterocyclic group and each of which groups is substituted with at least one group selected from the group consisting of a halogen atom and an alkoxy group, M represents a metal ion; n represents an integer of from 1 to 4; and $R_{a1}$, $R_{a2}$, $R_{a3}$, $R_{a4}$, $R_{a5}$ and $R_{a6}$ each represents a hydrogen atom or a substitutent.

7. The material for a luminescence element as claimed in claim 6, wherein $R_{e1}$ is an aryl group.

* * * * *